US011833284B2

(12) United States Patent
Ding et al.

(10) Patent No.: US 11,833,284 B2
(45) Date of Patent: Dec. 5, 2023

(54) SYSTEMS AND METHODS FOR BATCH SORBENT MATERIAL REUSE

(71) Applicants: Baxter International Inc., Deerfield, IL (US); Baxter Healthcare SA, Glattpark (CH)

(72) Inventors: Yuanpang Samuel Ding, Long Grove, IL (US); Rosa Hung-Chen Yeh, Libertyville, IL (US); Cristian Adolfo Menzel Bueno, Gurnee, IL (US); Ieng Kin Lao, Taipa (MO)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 251 days.

(21) Appl. No.: 17/231,230

(22) Filed: Apr. 15, 2021

(65) Prior Publication Data

US 2021/0228791 A1   Jul. 29, 2021

Related U.S. Application Data

(63) Continuation of application No. 16/203,104, filed on Nov. 28, 2018, now Pat. No. 11,090,421.

(51) Int. Cl.
*A61M 1/16* (2006.01)
*B01J 20/02* (2006.01)
*B01J 20/06* (2006.01)

(52) U.S. Cl.
CPC ........ *A61M 1/1696* (2013.01); *B01J 20/0211* (2013.01); *B01J 20/0292* (2013.01); *B01J 20/06* (2013.01)

(58) Field of Classification Search
CPC .......... A61M 1/1696; B01J 20/0211; B01J 20/0292; B01J 20/06; B01J 20/28052; B01J 2220/62
See application file for complete search history.

(56) References Cited

U.S. PATENT DOCUMENTS

| 4,391,964 A | 7/1983 | Wick et al. |
| 4,623,329 A | 11/1986 | Drobish et al. |

(Continued)

FOREIGN PATENT DOCUMENTS

| EP | 0311244 | 4/1989 |
| EP | 3269757 | 1/2018 |

(Continued)

OTHER PUBLICATIONS

Written Opinion for International Application No. PCT/US2019/063699 dated Oct. 9, 2020 (7 pages).

(Continued)

*Primary Examiner* — Dirk R Bass
(74) *Attorney, Agent, or Firm* — K&L Gates LLP

(57) ABSTRACT

Methods, sorbent cartridges and cleaning devices are disclosed for refurbishing sorbent materials. In one implementation among multiple implementations, a medical fluid delivery method includes: providing a sorbent cartridge including $H^+ZP$ within a casing for a treatment; and after the treatment, refurbishing the $H^+ZP$ while maintained within the casing via (i) regenerating the non-disinfected $H^+ZP$ by flowing an acid solution through the casing, (ii) rinsing the regenerated $H^+ZP$ while maintained within the casing, (iii) disinfecting the regenerated and rinsed $H^+ZP$ by flowing a disinfecting agent through the casing, and (iv) rinsing the regenerated and disinfected $H^+ZP$ while maintained within the casing. Multiple batch sorbent refurbishing implementations are also disclosed.

8 Claims, 10 Drawing Sheets

(56) References Cited

U.S. PATENT DOCUMENTS

| | | |
|---|---|---|
| 5,587,157 A | 12/1996 | Cox et al. |
| 6,332,985 B1 | 12/2001 | Sherman et al. |
| 9,682,184 B2 | 6/2017 | Wong |
| 9,707,329 B2 | 7/2017 | Merchant et al. |
| 2004/0191162 A1 | 9/2004 | Hai et al. |
| 2013/0123560 A1 | 5/2013 | Jacobson et al. |
| 2013/0260988 A1 | 10/2013 | Herfert et al. |
| 2014/0001112 A1 | 1/2014 | Karoor et al. |
| 2014/0336568 A1 | 11/2014 | Wong |
| 2015/0108069 A1 | 4/2015 | Merchant et al. |
| 2015/0251162 A1 | 9/2015 | Pudil et al. |
| 2015/0367055 A1 | 12/2015 | Pudil et al. |
| 2016/0243299 A1 | 8/2016 | Gerber et al. |
| 2016/0243541 A1 | 8/2016 | Menon et al. |
| 2018/0030604 A1 | 2/2018 | Manabe et al. |
| 2018/0177933 A1 | 6/2018 | Merchant |
| 2018/0214623 A1 | 8/2018 | Martin |
| 2020/0164339 A1 | 5/2020 | Yeh et al. |

FOREIGN PATENT DOCUMENTS

| | | |
|---|---|---|
| EP | 3326712 | 5/2018 |
| EP | 3415182 | 12/2018 |
| EP | 3546042 | 10/2019 |
| RU | 2137540 | 9/1999 |
| RU | 2401160 | 10/2010 |
| WO | 2003/042098 | 5/2003 |
| WO | 2009/157877 | 12/2009 |
| WO | 2011/125758 | 10/2011 |
| WO | 2015/060914 | 4/2015 |
| WO | 2015/199768 | 12/2015 |
| WO | 2015/199864 | 12/2015 |
| WO | 2016/191042 | 12/2016 |

OTHER PUBLICATIONS

IPRP for International Application No. PcT/US2019/063699 dated Feb. 3, 2021 (28 pages).
Transmittal of International Search Report and Written Opinion of the International Searching Authority for PCT/US2019/063699 dated Mar. 13, 2020 (19 pages).
Transmittal of International Search REport and Written Opinion of the International Searching Authority for PCT/US2019/063664 dated Feb. 21, 2020 (13 pages).
India Office Action dated Feb. 1, 2023 for App. No. 202117020646 (6 pages).

SYSTEMS AND METHODS FOR BATCH SORBENT MATERIAL REUSE

CROSS REFERENCE TO RELATED APPLICATIONS

This application is a continuation of U.S. application Ser. No. 16/203,104, filed Nov. 28, 2018, the entire contents of which are incorporated herein by reference for all purposes.

BACKGROUND

The present invention relates generally to medical fluid systems and more particularly to the operation and reuse of sorbent materials for dialysis.

One drawback for known hemodialysis machines that produce treatment fluid online or at the time of treatment is water usage. Hi-dose dialysis is preferred by certain clinicians, and may use 200 liters or more of water per treatment. 200 liters is a lot of water for a clinic and may be especially taxing for a home dialysis treatment, where water may be scarce and/or expensive. The equipment associated with purifying the water and the energy associated with heating that much water or dialysis fluid also add to the treatment cost.

Sorbent technology provides a solution to the high water usage of known online dialysis systems. Here, instead of discarding the used dialysis fluid exiting the dialyzer, the used dialysis fluid or effluent is pumped through a sorbent cartridge, which cleans the used dialysis fluid, removing toxic waste by-products from the used fluid. Infusate is pumped into the cleaned fluid to add back removed electrolytes and other constituents to restore the regenerated dialysis fluid to the same or similar chemical and physiological condition as fresh dialysis fluid.

Sorbent technology allows a same initial amount of water, e.g., ten liters or less, to be used over and over, to achieve the same or similar effective patient solute clearance as achieved under a single use hi-dose treatment. Thus, sorbent treatment can greatly reduce the amount of water needed for dialysis treatment.

Sorbent cartridges typically have multiple layers. The multiple layers may include (i) a mechanical purification layer that binds or removes heavy metals, oxidants and chloramines, (ii) a urease layer that converts urea removed from the patient into ammonium, (iii) a zirconium phosphate layer that binds or removes ammonium, calcium, magnesium, potassium and others, (iv) a zirconium oxide layer that binds or removes phosphate, chloride and heavy metals, and (v) an activated carbon layer that binds or removes creatinine, uric acid and middle molecules.

The materials of the sorbent layers may be expensive, especially the sorbent layers including zirconium phosphate and zirconium oxide. The cost of the sorbent cartridge may exceed the cost of treatment for single use hi-dose machines. It is accordingly desirable to reuse the materials of the sorbent column, especially the sorbent layers including zirconium phosphate and oxide. U.S. Pat. No. 9,707,329 ("the '329 Patent") describes routines for regenerating zirconium from a used sorbent cartridge. FIG. 2 from the '329 Patent shows that in the illustrated example, three different filtering and washing steps are required. The multiple washing and filtering steps are costly and labor intensive, and at some point, may cost more than the money saved in reusing the zirconium.

A need exists accordingly to provide an improved way to regenerate used sorbent column zirconium materials.

SUMMARY

The examples described herein disclose systems and methods to improve any treatment that uses sorbent materials to clean an effluent fluid. In particular, the systems and methods refurbish used sorbent materials, reducing the overall cost of the sorbent treatment. The treatment systems generally involve hemodialysis ("HD") systems. The HD systems of the present disclosure in various embodiments include a dialysis fluid circuit separated from a blood circuit by a dialyzer. The blood circuit includes one or more blood pump, e.g., a blood pump pumping along the arterial line. The blood circuit includes one or more air trap, e.g., an airtrap located in the venous line. The arterial line connects to a blood inlet of the dialyzer, while the venous line connects to a blood outlet of the dialyzer. Other blood circuit components are described herein.

The dialysis fluid circuit in an embodiment includes a fresh dialysis fluid pump pumping fresh and regenerated dialysis fluid to a dialysis fluid inlet of the dialyzer and a used dialysis fluid pump pumping used dialysis fluid from a dialysis fluid outlet of the dialyzer to and through a sorbent cartridge, which removes the waste products listed above and acquired from the patient's blood via transfer through semi-permeable membranes located within the dialyzer.

An infusate pump pumps infusate from an infusate source into the dialysis fluid circuit at a point downstream of the sorbent cartridge. The infusate replenishes the cleansed dialysis fluid, restoring the dialysis fluid into a form that may be pumped again to the dialyzer to treat the patient's blood.

The dialysis fluid circuit also includes a drain line, which enables used dialysis fluid at the end of treatment to be pumped to drain. Various valves are located in the blood and dialysis fluid circuits to control fluid flow as desired during treatment. All blood and dialysis fluid pumps and valves are operated under control of a control unit, which also accepts inputs from various sensors operating with the blood and dialysis fluid circuits, such as pressure sensors, conductivity sensors, air detection sensors, blood detection sensors, ammonia and other chemical sensors.

Structure and methodology are provided for removing a controlled amount of ultrafiltration ("UF") from the patient, such as a separate UF pump or one or more weigh scales outputting to the control unit. Volumetric UF control, such as balance chambers in the dialysis fluid circuit, may be provided alternatively. Any of the blood and dialysis fluid pumps and valves may be operated electrometrically, e.g., via peristaltic pumps and electrically actuated solenoid valves, or alternatively pneumatically, e.g., via volumetric pumps and pneumatic valves.

At the end of treatment using the above-described HD system, the sorbent cartridge is removed from the dialysis fluid circuit and at least some of the layers of material within the sorbent column are cleaned and regenerated according to the embodiments described below. It is contemplated to regenerate the sorbent materials in at least two different manners. In a first manner, the patient or caregiver collects the used sorbent cartridges. The collected used cartridges are either picked up or delivered periodically to a facility where they are cleaned and regenerated in a batch manner along with used sorbent materials from other patients. Here, the patient or caregiver receives a delivery of fresh sorbent cartridges periodically. In a second manner, at least a portion of the used sorbent cartridges are cleaned and regenerated onsite, either in a clinic or at home. In one example, any zirconium containing layers are cleaned and regenerated and then repacked into the sorbent column along with new single use layers. Single use layers in various embodiments include any one or more of a mechanical purification layer, a urease layer, an anion exchange layer and/or an activated carbon layer.

As discussed in detail below, the sorbent conditioning of the present disclosure may also be employed to refurbish used sorbent materials from peritoneal dialysis ("PD") systems and treatments.

With the above in mind, two primary embodiments are contemplated for cleaning and regenerating at least a portion of the sorbent layers, such as the zirconium containing layers.

Batch Refurbishing

In one primary embodiment, sorbent material refurbishing is performed in a batch operation in which used sorbent materials from multiple sorbent cartridges are combined and cleaned together. The sorbent refurbishing process in one embodiment provides an adequate ammonium removal capacity of zirconium phosphate containing greater than 90% sodium or hydrogen exchange sites. The sorbent refurbishing in various implementations involves the use of a disinfecting agent in combination with an acid, base or sodium salt treatment. The sorbent refurbishing is applicable to sorbent cartridges having different zirconium containing compartments provided in a serial (e.g., layered) or parallel (e.g., used dialysis fluid flows through one or the other compartment) configuration.

It is contemplated to provide the batch sorbent refurbishing process in any one of several different implementations of the first primary embodiment. In each case, used zirconium containing sorbent materials from multiple sorbent cartridges for a single or multiple patients are collected at a refurbishing facility. The total batch to be refurbished in one procedure may be in the range of 10 lbs. to 10000 lbs. In a first implementation, (i) non-disinfected zirconium phosphate ("ZP") is refurbished using an acid solution, (ii) the regenerated ZP is disinfected using a disinfecting agent, (iii) the disinfected and acid regenerated ZP is washed and filtered, (iv) the washed ZP is titrated to a desired pH, for example between and including 5.5 to 8.5, (v) the titrated ZP is washed and filtered to a conductivity below 50 µS/cm, (vi) the washed ZP is dried, e.g., in a vacuum oven, and (vii) the dried ZP is sieved using one or more sieves for one or more sorbent uses. The ZP is now ready to be reused.

In a second implementation, the titration and second washing procedures above are removed, such that non-disinfected zirconium phosphate ("ZP") is (i) regenerated using an acid solution, (ii) disinfected using a disinfecting agent, (iii) washed and filtered, (iv) dried, e.g., in a vacuum oven, and (v) sieved using one or more sieves for one or more sorbent uses. The ZP is now ready to be reused.

In a third implementation, the acid solution of the first implementation is replaced with a sodium based alkaline solution or a sodium salt solution, such that (i) non-disinfected zirconium phosphate ("ZP") is regenerated using a sodium based alkaline solution or a sodium salt solution, (ii) the regenerated ZP is disinfected using a disinfecting agent, (iii) the disinfected and sodium regenerated ZP is washed and filtered, (iv) the washed ZP is titrated to a desired pH, for example between and including 5.5 to 8.5, (v) the titrated ZP is washed and filtered to a conductivity below 50 µS/cm, (vi) the washed ZP is dried, e.g., in a vacuum oven, and (vii) the dried ZP is sieved using one or more sieves for one or more sorbent uses. The ZP is now ready to be reused.

In a fourth implementation, the acid solution of the second implementation is replaced with a sodium based alkaline solution or a sodium salt solution, such that (i) non-disinfected zirconium phosphate ("ZP") is regenerated using a sodium based alkaline solution or a sodium salt solution, (ii) the regenerated ZP is disinfected using a disinfecting agent, (iii) the disinfected and sodium regenerated ZP is washed and filtered, (iv) the washed ZP is dried, e.g., in a vacuum oven, and (v) the dried ZP is sieved using one or more sieves for one or more sorbent uses. The ZP is now ready to be reused.

In a fifth implementation, the regenerating and disinfecting procedures of the third implementation are reversed, such that (i) non-regenerated ZP is disinfected using a disinfecting agent, (ii) disinfected zirconium phosphate ("ZP") is regenerated using a sodium based alkaline solution or a sodium salt solution, (iii) the disinfected and sodium regenerated ZP is washed and filtered, (iv) the washed ZP is titrated to a desired pH, for example between and including 5.5 to 8.5, (v) the titrated ZP is washed and filtered to a conductivity below 50 µS/cm, (vi) the washed ZP is dried, e.g., in a vacuum oven, and (vii) the dried ZP is sieved using one or more sieves for one or more sorbent uses. The ZP is now ready to be reused.

In a sixth implementation, the regenerating and disinfecting procedures of the fourth embodiment are revered, such that (i) non-regenerated ZP is disinfected using a disinfecting agent, (ii) disinfected zirconium phosphate ("ZP") is regenerated using a sodium based alkaline solution or a sodium salt solution, (iii) the disinfected and sodium regenerated ZP is washed and filtered, (iv) the washed ZP is dried, e.g., in a vacuum oven, and (v) the dried ZP is sieved using one or more sieves for one or more sorbent uses. The ZP is now ready to be reused.

In any of the above implementations, the disinfecting agent may contain different types of chemicals. In one example, the chemical is sodium based, such as NaOCl in isopropyl alcohol ("IPA"). In another example, the chemical is a hydrogen based chemical, such as HOCl in IPA. A third example includes IPA as the primary disinfecting agent. Also, any of the above embodiments for preparing ZP for reuse is applicable to other zirconium containing materials, such as zirconium oxide ("ZO") and to different types of ZP, such as $H^+ZP$ and $Na^+ZP$. Additionally, the acid solution may be HCl, $H_2SO_4$, $H_3PO_4$, $HNO_3$ or acetic acid, and the sodium based alkaline solution or a sodium salt solution may be NaOH, $NaHCO_3$, $Na_2CO_3$ or NaCl.

The ZP made ready for reuse via any of the implementations above is placed within the column of a sorbent cartridge, e.g., in serial or parallel fashion with other zirconium containing materials, and with reused and/or new non-zirconium layers, such as mechanical filtration, urease and activated carbon layers. The layers form a refurbished sorbent cartridge that is deliverable to the patient along with other refurbished cartridges to be used over multiple treatments.

Onsite Refurbishing

In a second primary embodiment, sorbent material refurbishing is performed in an onsite operation in which at least the zirconium containing materials (e.g., ZO, $H^+ZP$ and $Na^+ZP$) are conditioned for reuse. As with the previous primary embodiment, the sorbent refurbishing process of the second primary embodiment may provide an adequate ammonium removal capacity of zirconium phosphate containing greater than 90% sodium or hydrogen exchange sites. The sorbent refurbishing cleaning in various implementations again involves the use of a disinfecting agent in combination with an acid, base or sodium salt treatment. The sorbent refurbishing is applicable to sorbent cartridges having different zirconium containing compartments provided in a serial (e.g., layered) or in parallel (e.g., used dialysis fluid flows through one or the other compartment).

A major difference between the first and second primary embodiments is that in the batch process, the sorbent materials are removed from their layering casing, so that the materials from multiple sorbent cartridges may be mixed together and refurbished at once. In the onsite embodiment, on the other hand, the sorbent materials are left to reside within their casing, for ease of handling and so that the patient or caregiver does not have to handle the sorbent materials directly.

Another difference between the first and second primary embodiments may be that the same conditioning implementations are used for both $H^+ZP$ and $Na^+ZP$ in the first primary embodiment, while a first conditioning implementation is used for $H^+ZP$ versus a second conditioning implementation used for $Na^+ZP$ in the second primary embodiment. It should be appreciated however that the reverse may be true, namely, different conditioning implementations may be developed for $H^+ZP$ versus $Na^+ZP$ for the batch embodiment, while the same conditioning implementation may be developed for $H^+ZP$ and $Na^+ZP$ for the onsite embodiment.

It is contemplated to provide the onsite sorbent refurbishing cleaning process in any one of several different implementations. In each case, used zirconium containing sorbent layer casings are removed from the patient's sorbent cartridge along with the non-zirconium layer casings (e.g., mechanical filtration casing, urease casing and activated carbon casing(s)). The non-zirconium layer casings may also be conditioned for reuse or discarded.

In a first implementation, which may be specific to conditioning $H^+ZP$, (i) non-disinfected $H^+ZP$ is regenerated within its casing in a reverse flow direction, such that the casing inlet during treatment becomes the casing outlet during regeneration and vice versa, using an acid solution through the casing at a flow rate of for example 0.1 ml/min to 5 ml/min and at a temperature from about 20° C. to about 80° C., which may be performed until the pH of the eluent (acid used to contact $H^+ZP$) equals or approaches the pH of the incoming acid solution, (ii) water is rinsed through the regenerated $H^+ZP$ within its casing (e.g., in the reverse flow direction) until conductivity of the effluent (water used to wash regenerated $H^+ZP$) reaches a conductivity of 100 µS/cm or less, (iii) the regenerated and rinsed $H^+ZP$ is disinfected via a disinfecting agent (which may contain a hydrogen based chemical such as HOCl in IPA) flowed, e.g., pumped, through the $H^+ZP$ casing (e.g., in the reverse flow direction); and (iv) flow is reversed and water is rinsed through the regenerated and disinfected $H^+ZP$ though its casing in the normal treatment flow direction until conductivity of the eluent (water used to wash regenerated and disinfected $H^+ZP$) reaches a conductivity of 100 µS/cm or less. The $H^+ZP$ casing, e.g., after drying, is ready to be reintroduced into the sorbent cartridge and reused.

In a second implementation, which may be specific to conditioning $Na^+ZP$, (i) non-disinfected $Na^+ZP$ is regenerated within its casing in a reverse flow direction, such that the casing inlet during treatment becomes the casing outlet during regeneration and vice versa, and a sodium based alkaline solution or a sodium salt solution is flowed, e.g., pumped, through the casing at a flow rate of for example 0.1 ml/min to 5 ml/min and at a temperature from about 20° C. to about 80° C., which may be performed until the conductivity of the conductivity of the eluent (sodium solution used to contact $Na^+ZP$) equals or approaches the conductivity of the incoming sodium solution, (ii) water is rinsed through the regenerated $Na^+ZP$ within its casing (e.g., in the reverse flow direction,) for a determined time (conductivity already controlled in (i)), (iii) the regenerated and rinsed $Na^+ZP$ is disinfected via a disinfecting agent (may contain a sodium based chemical such as NaOCl in IPA) flowed, e.g., pumped, through the $Na^+ZP$ casing (e.g., in the reverse flow direction); and (iv) flow is reversed and water is rinsed through the regenerated and disinfected $Na^+ZP$ casing in the normal treatment flow direction until conductivity of the eluent (water used to wash regenerated and disinfected $Na^+ZP$) reaches a conductivity of 100 µS/cm or less. The $Na^+ZP$ casing, e.g., after drying, is ready to be reintroduced into the sorbent cartridge and reused.

In a third implementation, which may also be specific to conditioning $Na^+ZP$, the regeneration and disinfection procedures of the second implementation are reversed, such that (i) used and non-regenerated $Na^+ZP$ is disinfected within its casing in a normal treatment or reverse flow direction using a disinfecting agent that may contain a sodium based chemical such as NaOCl in IPA, (ii) water is rinsed through the disinfected $Na^+ZP$ within its casing (in normal treatment or reverse flow direction) to remove residual chemicals until the conductivity of the eluent (water used to wash disinfected $Na^+ZP$) reaches a conductivity of 100 µS/cm or less; (iii) disinfected $Na^+ZP$ is regenerated within its casing in the reverse flow direction, such that the casing inlet during treatment becomes the casing outlet during regeneration and vice versa, and a sodium based alkaline solution or a sodium salt solution is flowed, e.g., pumped, through the casing at a flow rate of for example 0.1 ml/min to 5 ml/min and at a temperature from about 20° C. to about 80° C., which may be performed until the conductivity of the eluent (sodium solution used to contact $Na^+ZP$) equals or almost equals the conductivity of the incoming sodium solution; and (iv) flow is reversed and water is rinsed through the disinfected and regenerated $Na^+ZP$ though its casing in the normal treatment flow direction, e.g., for a determined amount of time (conductivity already controlled in (ii) and (iii)). The $Na^+ZP$ casing, e.g., after drying, is now ready to be reintroduced into the sorbent cartridge and reused.

Once any or all of the $H^+ZP$ and $Na^+ZP$ casings are conditioned for reuse, the patient or caregiver inserts the reusable casings into the sorbent cartridge along with any additional casings, e.g., mechanical filtration casing, urease casing and/or activated carbon casing(s), which may themselves have been conditioned for reuse or opened from a sterile package as a new casing. The patient or caregiver inserts the casings in a proper order and orientation, which may be aided by markings provided on the outside of sorbent cartridge. Alternatively or additionally, the cartridge and casings may be somewhat conical in shape so that the casings only fit snugly within the cartridge when stacked in the proper order and orientation.

In an embodiment, the sorbent cartridge is closed at one end, e.g., the outlet end, and openable at the other end, e.g., the inlet end, such that the user (e.g., patient, caregiver, clinician or technician) in one embodiment only has to (i) open one side of the cartridge to remove all inner sorbent casings, (ii) condition the casings to be reused, (iii) replace the casings to be discarded, (iv) rinse the cartridge itself, (v) reinsert the refurbished and new casings into the rinsed cartridge, and (vi) close the opened end of the cartridge. In various embodiments, the inlet lid or cap may thread onto the remainder of the cartridge housing or be held removeably fixed to the housing via releasable clips, such as spring clips. In either case, it is contemplated that the action of applying the lid or cap to the remainder of the cartridge in turn compresses the sorbent casings together, compressing seals (e.g., o-ring seals) between the casings, such that patient effluent cannot leak between the casings and the inner cartridge. The seals may be captured and carried by the casings for ease of handling when the casings are removed from the sorbent cartridge.

The onsite operation may be performed in a dialysis clinic, at a hospital, or at a patient's home, for example. At a clinic, the sorbent casing removal and replacement may be performed by a clinician or technician. At a hospital, the sorbent casing removal and replacement may be performed by a nurse or technician. At home, the sorbent casing removal and replacement may be performed by the patient or a caregiver for the patient.

It is further contemplated to provide at the clinic, hospital, patient's home or offsite one or more sorbent conditioning or refurbishing device. The device may be configured to condition or refurbish (i) one sorbent casing at a time, (ii) multiple sorbent casings of a same type at the same time, (iii) multiple sorbent casings of different types at the same time, (iv) multiple sorbent casings of a same type sequentially, or (v) multiple sorbent casings of different types sequentially. The sorbent conditioning or refurbishing device accepts the one or more sorbent casing in a sealed manner, conditions or refurbishes the one or more sorbent casing according to any of the implementations discussed above for the onsite primary embodiment, and informs the user when the casing is ready to be removed from the conditioning or refurbishing device and reused.

In light of the disclosure herein and without limiting the disclosure in any way, in a first aspect of the present disclosure, which may be combined with any other aspect listed herein unless specified otherwise, a medical fluid delivery method includes providing a sorbent cartridge including zirconium phosphate ("ZP") or zirconium oxide ("ZO") for a treatment; and after the treatment, refurbishing the ZP or ZO via the steps of (i) regenerating the non-disinfected ZP or ZO using an acid solution, (ii) disinfecting the regenerated ZP or ZO using a disinfecting agent, (iii) at least one of washing or filtering the regenerated and disinfected ZP or ZO, (iv) titrating the washed or filtered ZP or ZO to a desired pH, (v) at least one of washing or filtering the titrated ZP or ZO until a desired conductivity is reached, (vi) drying the rewashed or refiltered ZP or ZO, and (vii) sieving the dried ZP or ZO.

In a second aspect of the present disclosure, which may be combined with any other aspect listed herein unless specified otherwise, at least one of (a) the acid solution is HCl, $H_2SO_4$, $H_3PO_4$, $HNO_3$ or acetic acid or (b) the disinfecting agent (i) is sodium based, such as including NaOCl, (ii) is hydrogen based, such as including HOCl, or (iii) includes isopropyl alcohol ("IPA").

In a third aspect of the present disclosure, which may be combined with any other aspect listed herein unless specified otherwise, the desired pH is between and including 5.5 to 8.5.

In a fourth aspect of the present disclosure, which may be combined with any other aspect listed herein unless specified otherwise, the desired conductivity is below 50 μS/cm.

In a fifth aspect of the present disclosure, which may be combined with any other aspect listed herein unless specified otherwise, refurbishing the ZP or ZO includes combining ZP or ZO removed from multiple sorbent cartridges before regeneration.

In a sixth aspect of the present disclosure, which may be combined with any other aspect listed herein unless specified otherwise, a medical fluid delivery method includes providing a sorbent cartridge including zirconium phosphate ("ZP") or zirconium oxide ("ZO") for a treatment; and after the treatment, refurbishing the ZP or ZO via (i) regenerating the non-disinfected ZP or ZO using an acid solution, (ii) disinfecting the regenerated ZP or ZO using a disinfecting agent, (iii) at least one of washing or filtering the regenerated and disinfected ZP or ZO, (iv) drying the washed or filtered ZP or ZO, and (v) sieving the dried ZP or ZO.

In a seventh aspect of the present disclosure, which may be combined with the sixth aspect and any other aspect listed herein unless specified otherwise, at least one of (a) the acid solution is HCl, $H_2SO_4$, $H_3PO_4$, $HNO_3$ or acetic acid or (b) the disinfecting agent (i) is sodium based, such as including NaOCl, (ii) is hydrogen based, such as including HOCl, or (iii) includes isopropyl alcohol ("IPA").

In an eighth aspect of the present disclosure, which may be combined with the sixth aspect and any other aspect listed herein unless specified otherwise, refurbishing the ZP or ZO includes combining ZP or ZO removed from multiple sorbent cartridges before regeneration.

In a ninth aspect of the present disclosure, which may be combined with any other aspect listed herein unless specified otherwise, a medical fluid delivery method includes providing a sorbent cartridge including zirconium phosphate ("ZP") or zirconium oxide ("ZO") for a treatment; and after the treatment, refurbishing the ZP or ZO via (i) regenerating the non-disinfected ZP or ZO using a sodium based alkaline solution or a sodium salt solution, (ii) disinfecting the regenerated ZP or ZO using a disinfecting agent, (iii) at least one of washing or filtering the regenerated and disinfected ZP or ZO, (iv) titrating the washed or filtered ZP or ZO to a desired pH, (v) at least one of washing or filtering the titrated ZP or ZO until a desired conductivity is reached, (vi) drying the rewashed or refiltered ZP or ZO, and (vii) sieving the dried ZP or ZO.

In a tenth aspect of the present disclosure, which may be combined with the ninth aspect and any other aspect listed herein unless specified otherwise, at least one of (a) the sodium based alkaline solution or a sodium salt solution is NaOH, $NaHCO_3$, $Na_2CO_3$ or NaCl or (b) the disinfecting agent (i) is sodium based, such as including NaOCl, (ii) is hydrogen based, such as including HOCl, or (iii) includes isopropyl alcohol ("IPA").

In an eleventh aspect of the present disclosure, which may be combined with the ninth aspect and any other aspect listed herein unless specified otherwise, the desired pH is between and including 5.5 to 8.5.

In a twelfth aspect of the present disclosure, which may be combined with the ninth aspect and any other aspect listed herein unless specified otherwise, the desired conductivity is below 50 μS/cm.

In a thirteenth aspect of the present disclosure, which may be combined with the ninth aspect and any other aspect listed herein unless specified otherwise, refurbishing the ZP or ZO includes combining ZP or ZO removed from multiple sorbent cartridges before regeneration.

In a fourteenth aspect of the present disclosure, which may be combined with any other aspect listed herein unless specified otherwise, a medical fluid delivery method includes providing a sorbent cartridge including zirconium phosphate ("ZP") or zirconium oxide ("ZO") for a treatment; and after the treatment, refurbishing the ZP or ZO via (i) regenerating the non-disinfected ZP or ZO using a sodium based alkaline solution or a sodium salt solution, (ii) disinfecting the regenerated ZP or ZO using a disinfecting agent, (iii) at least one of washing or filtering the regenerated and disinfected ZP or ZO, (iv) drying the washed or filtered ZP or ZO, and (v) sieving the dried ZP or ZO.

In a fifteenth aspect of the present disclosure, which may be combined with the fourteenth aspect and any other aspect listed herein unless specified otherwise, at least one of (a) the sodium based alkaline solution or a sodium salt solution is NaOH, $NaHCO_3$, $Na_2CO_3$ or NaCl or (b) the disinfecting agent (i) is sodium based, such as including NaOCl, (ii) is hydrogen based, such as including HOCl, or (iii) includes isopropyl alcohol ("IPA").

In a sixteenth aspect of the present disclosure, which may be combined with the fourteenth aspect and any other aspect listed herein unless specified otherwise, refurbishing the ZP or ZO includes combining ZP or ZO removed from multiple sorbent cartridges before regeneration.

In a seventeenth aspect of the present disclosure, which may be combined with any other aspect listed herein unless specified otherwise, a medical fluid delivery method includes providing a sorbent cartridge including zirconium phosphate ("ZP") or zirconium oxide ("ZO") for a treatment; and after the treatment, refurbishing the ZP or ZO via (i) disinfecting the non-regenerated ZP or ZO using a disinfecting agent, (ii) regenerating the disinfected ZP or ZO using a sodium based alkaline solution or a sodium salt solution, (iii) at least one of washing or filtering the disinfected and regenerated ZP or ZO, (iv) titrating the washed or filtered ZP or ZO to a desired pH, (v) at least one of washing or filtering the titrated ZP or ZO until a desired conductivity is reached, (vi) drying the rewashed or refiltered ZP or ZO, and (vii) sieving the dried ZP or ZO.

In an eighteenth aspect of the present disclosure, which may be combined with the seventeenth aspect and any other aspect listed herein unless specified otherwise, at least one of (a) the sodium based alkaline solution or a sodium salt solution is NaOH, $NaHCO_3$, $Na_2CO_3$ or NaCl or (b) the disinfecting agent (i) is sodium based, such as including NaOCl, (ii) is hydrogen based, such as including HOCl, or (iii) includes isopropyl alcohol ("IPA").

In a nineteenth aspect of the present disclosure, which may be combined with the seventeenth aspect and any other aspect listed herein unless specified otherwise, the desired pH is between and including 5.5 to 8.5.

In a twentieth aspect of the present disclosure, which may be combined with the seventeenth aspect and any other aspect listed herein unless specified otherwise, the desired conductivity is below 50 µS/cm.

In a twenty-first aspect of the present disclosure, which may be combined with the seventeenth aspect and any other aspect listed herein unless specified otherwise, refurbishing the ZP or ZO includes combining ZP or ZO removed from multiple sorbent cartridges before disinfection.

In a twenty-second aspect of the present disclosure, which may be combined with any other aspect listed herein unless specified otherwise, a medical fluid delivery method includes providing a sorbent cartridge including zirconium phosphate ("ZP") or zirconium oxide ("ZO") for a treatment; and after the treatment, refurbishing the ZP or ZO via (i) disinfecting the non-regenerated ZP or ZO using a disinfecting agent, (ii) regenerating the disinfected ZP or ZO using a sodium based alkaline solution or a sodium salt solution, (iii) at least one of washing or filtering the disinfected and regenerated ZP or ZO, (iv) drying the washed or filtered ZP or ZO, and (v) sieving the dried ZP or ZO.

In a twenty-third aspect of the present disclosure, which may be combined with the twenty-second aspect and any other aspect listed herein unless specified otherwise, at least one of (a) the sodium based alkaline solution or a sodium salt solution is NaOH, $NaHCO_3$, $Na_2CO_3$ or NaCl or (b) the disinfecting agent (i) is sodium based, such as including NaOCl, (ii) is hydrogen based, such as including HOCl, or (iii) includes isopropyl alcohol ("IPA").

In a twenty-fourth aspect of the present disclosure, which may be combined with the twenty-second aspect and any other aspect listed herein unless specified otherwise, refurbishing the ZP or ZO includes combining ZP or ZO removed from multiple sorbent cartridges before disinfection.

In a twenty-fifth aspect of the present disclosure, any of the structure and functionality disclosed in connection with FIGS. 1 to 15 may be included or combined with any of the other structure and functionality disclosed in connection with FIGS. 1 to 15.

In light of the present disclosure and the above aspects, it is therefore an advantage of the present disclosure to provide an improved used sorbent material regeneration system and method.

It is another advantage of the present disclosure to provide an improved used sorbent material regeneration system and method operable in a batch manner.

It is a further advantage of the present disclosure to provide an improved used sorbent material regeneration system and method that is operable onsite.

It is still another advantage of the present disclosure to provide a sorbent cartridge that is readily disassembled and reassembled to remove used sorbent material casings and replace refurbished or new sorbent material casings.

It is a further advantage of the present disclosure to provide an improved used sorbent material regeneration system and method having a sorbent conditioning or refurbishing device that accepts used sorbent material casings and generates refurbished sorbent material casings.

The advantages discussed herein may be found in one, or some, and perhaps not all of the embodiments disclosed herein. Additional features and advantages are described herein, and will be apparent from, the following Detailed Description and the figures.

DETAILED DESCRIPTION

System Overview

Figure 1:
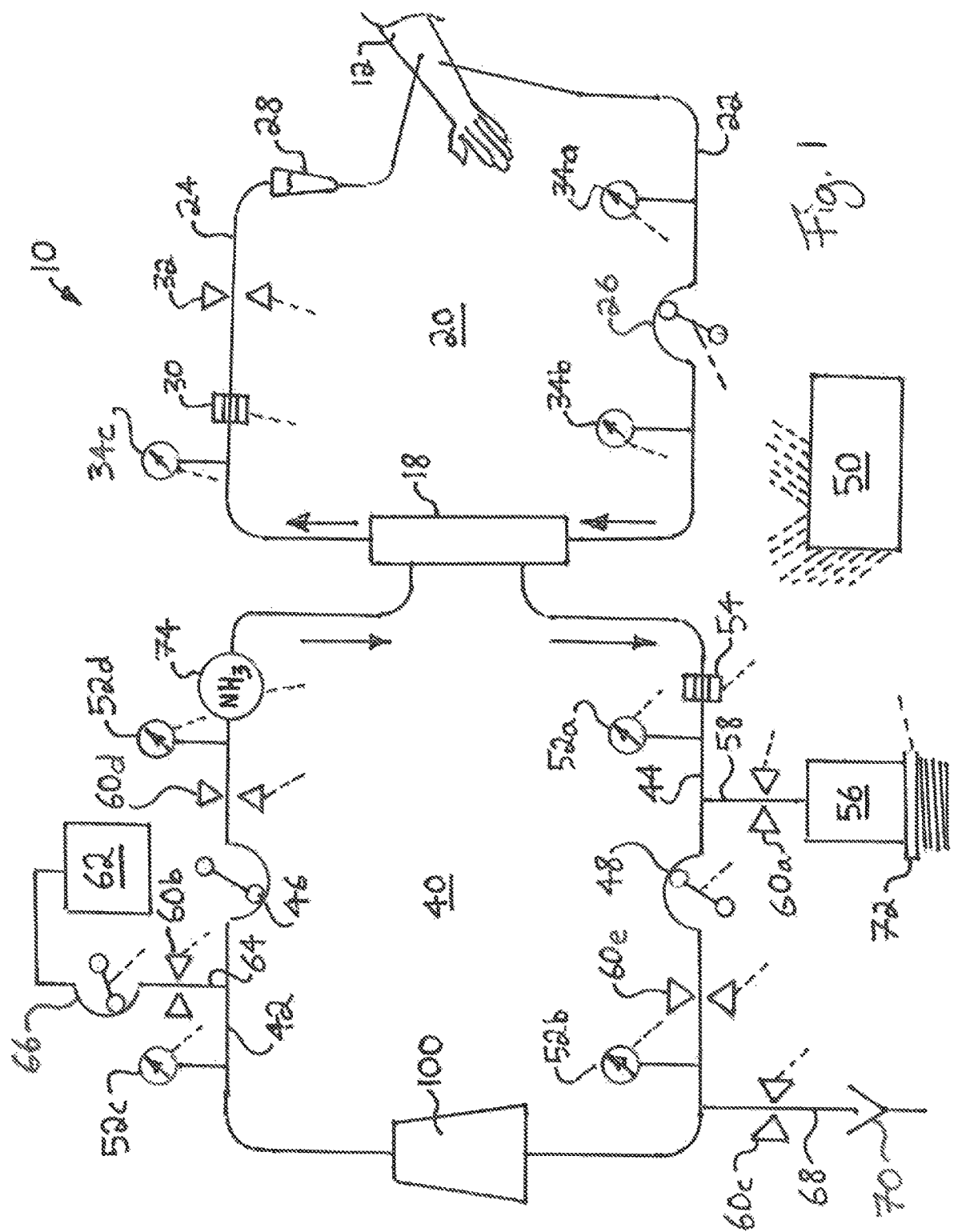
FIG. 1 is a schematic view of one embodiment of a sorbent hemodialysis ("HD") system that may employ any of the sorbent refurbishing techniques of the present disclosure.

Referring now to the drawings and in particular to FIG. 1, a medical fluid delivery system, such as a hemodialysis ("HD") system 10 is illustrated. In the illustrated embodiment, HD system 10 includes a blood circuit 20 separated from a dialysis fluid circuit 40 by a dialyzer 18. Blood circuit 20 connects to the vascular system of patient 12. In particular, blood circuit 20 includes an arterial line 22 having an arterial needle that allows blood to be removed from patient 12. Arterial line 22 runs to an inlet of the blood compartment of dialyzer 18. Blood circuit 20 also includes a venous line 24 having an venous needle that allows blood cleansed via dialyzer 18 to be retuned to patient 12. Venous line 24 runs to an outlet of the blood compartment of dialyzer 18.

In the illustrated embodiment, a blood pump 26 is provided along arterial line 22. Blood pump 26 removes blood from patient 12 via arterial line 22 under negative pressure and pumps the blood under positive pressure through the reminder of the arterial line, the blood compartment of dialyzer 18, and venous line 24, back to patient 12. Blood pump 26 may be an electromechanical peristaltic pump or a volumetric or diaphragm pump, e.g., driven via pneumatic pressure. Blood circuit 20 includes one or more air trap, e.g., airtrap 28, located in venous line 24, to remove any air from the blood before it is returned to patient 12. A venous line air detector 30 and occluder or valve 32 are provided to clamp or occlude venous line 24 in the case that air is detected via air detector 30. Pressure sensors 34a to 34c are provided to monitor arterial line negative pressure, arterial line positive pressure and venous line positive pressure, respectively. Blood circuit 20 may also include a hematocrit or blood consistency sensor (not illustrated).

FIG. 1 further illustrates that dialysis fluid circuit 40 includes a fresh dialysis fluid line 42, which delivers fresh dialysis fluid (e.g., dialysis fluid cleansed via sorbent cartridge 100) to an inlet of a dialysis fluid compartment of dialyzer 18. Dialysis fluid circuit 40 includes a used dialysis fluid line 44, which removes used dialysis fluid from an outlet of the dialysis fluid compartment of dialyzer 18. Sorbent cartridge 100 separates fresh dialysis fluid line 42 from used dialysis fluid line 44. One or both of the fresh and used dialysis fluid lines may be provided with a pump. In the illustrated embodiment, a fresh dialysis fluid pump 46 operates with or along fresh dialysis fluid line 42, while used dialysis fluid pump 48 operates with or along used dialysis fluid line 44. Fresh and used dialysis fluid pumps 46 and 48 may be electromechanical peristaltic pumps or volumetric or diaphragm pumps, e.g., driven via pneumatic pressure.

Pressure sensors 52a to 52d are located along dialysis fluid circuit 40 to detect, respectively, (a) negative pressure between dialyzer 18 and used dialysis fluid pump 48, (b) positive pressure between used dialysis fluid pump 48 and sorbent cartridge 100, (c) negative pressure between sorbent cartridge 100 and fresh dialysis fluid pump 46, and (d) positive pressure between fresh dialysis fluid pump 46 and dialyzer 18. A blood leak detector 54 is located in used dialysis fluid line 44 just downstream of dialyzer 18 to look for leaks in the hollow fiber microporous membranes of the dialyzer 18. An ammonia sensor 74 (and/or other physiological sensor) is located along fresh dialysis fluid line 42 and is used to ensure that regenerated dialysis fluid from sorbent cartridge 100 will be effective to remove toxins from patient 12 when returned to the patient.

An initial fluid supply and UF container 56 is connected fluidly via line 58 to used dialysis fluid line 44 upstream of used dialysis fluid pump 48. Used dialysis fluid pump 48 pulls an initial supply of dialysis fluid from container 56 into dialysis fluid circuit 40 to prime the circuit and then for use to clean the blood of patient 12. The initial supply of HD dialysis fluid is prepared in one embodiment by administering liquid or dried HD concentrate (e.g., acid and bicarbonate) into container 56 and then pouring a specified amount of potable water, e.g., six to ten liters, into container 56 to mix (and dissolve if needed) the concentrate. Pumps 46 and 48 are operated to pump the initial supply of dialysis fluid through sorbent cartridge 100 to purify the initial supply to an appropriate level before the initial supply reaches dialyzer 18. A valve 60a is located along supply line 58 to selectively allow or not allow initial fluid supply and UF container 56 to communicate fluidly with dialysis fluid circuit 40.

An infusate container 62 is connected fluidly via line 64 to fresh dialysis fluid line 42 downstream of sorbent cartridge 100. An infusate pump 66, such as a peristaltic or a volumetric pump, is located along infusate line 64 between infusate container 62 and fresh dialysis fluid line 42. Sorbent cartridge 100 also absorbs desirable components that need to be repleneshed. Infusate pump 66 meters a desired amount of infusate (containing electrolytes and other constituents) that places the dialysis fluid regenerated via sorbent cartridge 100 in the same or similar chemical and physiological condition as fresh dialysis fluid from container 56. A valve 60b is located along infusate line 64 to selectively allow or not allow infusate container 62 to communicate fluidly with dialysis fluid circuit 40.

In the illustrated embodiment, dialysis fluid circuit 40 includes a drain line 68, which extends from used dialysis fluid line 44 and enables used dialysis fluid at the end of treatment to be pumped to a drain 70, such as a drain bag or a house drain (e.g., a toilet or bath tub). A valve 60c is located along drain line 68, which along with valves 60d and 60e, selectively allows or occludes flow through the drain line to drain 70.

Valves 60d and 60e are located in fresh dialysis fluid line 42 and used dialysis fluid line 44, respectively, to selectively allow or occlude flow through those lines. Any valve discussed herein, including any of valves 60a to 60e may be an electrically actuated solenoid pinch valve that operates directly with the associated tube or line or be a disposable-cassette based valve that is opened or closed pneumatically or electromechanically.

Structure and methodology are provided for removing a controlled amount of ultrafiltration ("UF") from patient 12, such as a separate UF pump or one or more weigh scales outputting to control unit 50. In the illustrated embodiment, a weigh scale 72 is located beneath initial fluid supply and UF container 56. Weigh scale 72 at the beginning of treatment weighs the initial supply of fresh dialysis fluid within container 56 to know that the fresh dialysis fluid has been proportioned properly with the amount of wet or dry dialysis fluid concentrate provided and delivered into fresh dialysis fluid supply container 56. During treatment, valves 60a and 60e are toggled periodically to enable a prescribed amount of used dialysis fluid to be diverted as UF into now UF container 56, wherein the prescribed amount is obtained using weigh scale 72. At the end of treatment, the remaining used dialysis fluid is delivered instead to drain 70 via drain line 68 and drain valve 60c. Other types of volumetric control, such as balance chambers in dialysis fluid circuit 40 may be used alternatively to control UF and the amount of fresh and used dialysis fluid delivered to and removed from dialyzer 18.

In the illustrated embodiment as indicated by the dashed electrical and/or signal lines, all blood and dialysis fluid pumps and valves (such as valves 32 and 60a to 60e) are operated under control of a control unit 50, which also accepts inputs from each of the sensors described above operating with blood circuit 20 and dialysis fluid circuit 40, such as, pressure sensors 34a to 34c and 52a to 52d, conductivity sensors, air detection sensor 30, blood detection sensor 54, ammonia 74 and/or other chemical sensors.

At the end of treatment using above-described HD system 10, sorbent cartridge 100 is removed from dialysis fluid circuit 40 and at least some of the layers of material within a sorbent column of the cartridge are cleaned and regenerated according to the embodiments described below.

Figure 2:
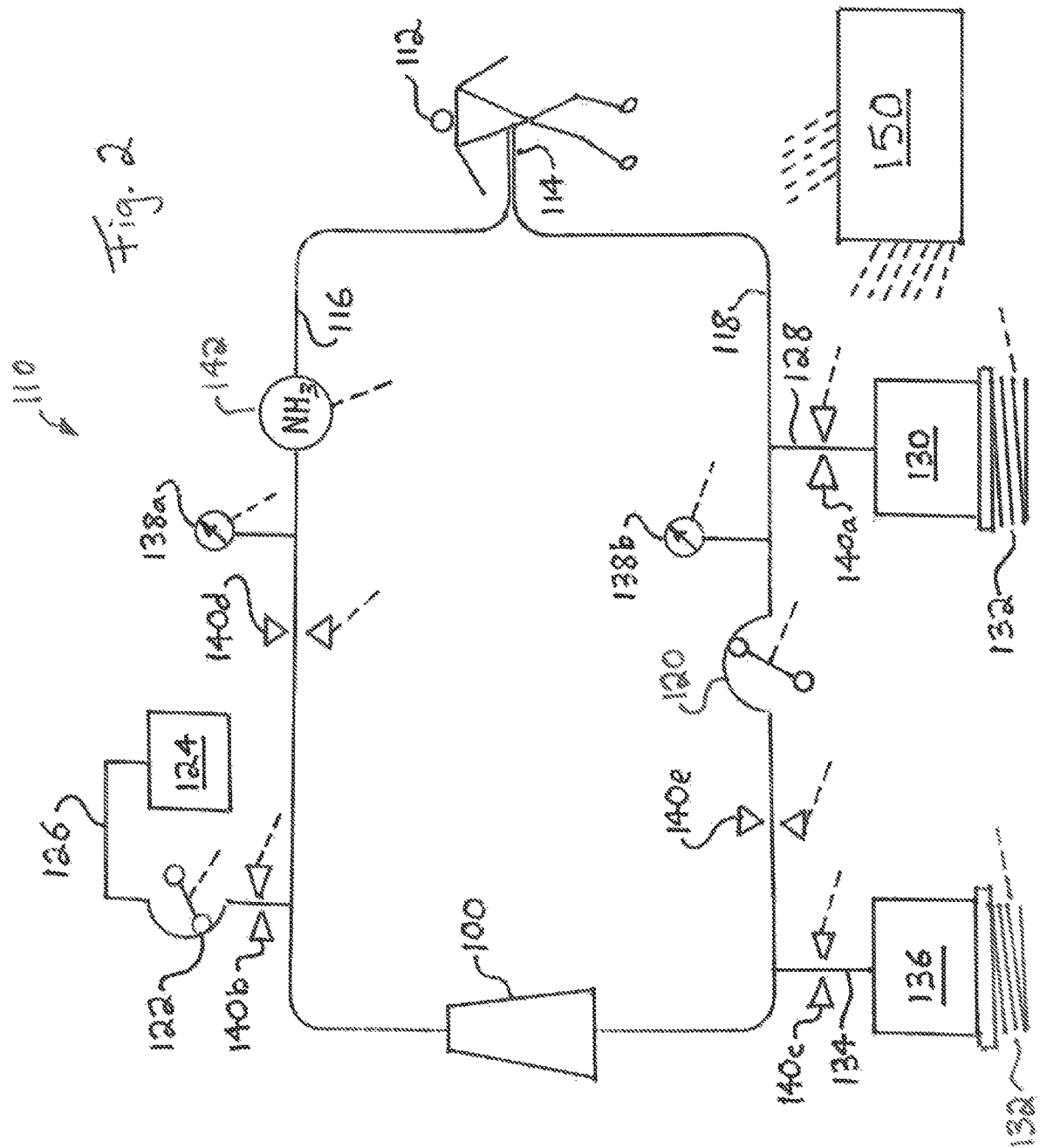
FIG. 2 is a schematic view of one embodiment of a sorbent peritoneal dialysis ("PD") system that may employ any of the sorbent refurbishing techniques of the present disclosure.

Referring now to FIG. 2, the sorbent conditioning of the present disclosure may also be employed to refurbish used sorbent materials from peritoneal dialysis ("PD") treatments using a PD system, such as PD system 110. PD system 110 operates with a patient 112. In system 110, dialyzer 18 is not used, however, sorbent column 100 is used. PD system 110 is described as a continuous flow peritoneal dialysis ("CFPD"), however, the sorbent cleaning of the present disclosure is equally applicable to continuous cycling peritoneal dialysis ("CCPD") and tidal PD. With CFPD, patient 112 is provided with a dual lumen catheter 114, which allows fresh or regenerated dialysis fluid to be pumped along fresh dialysis fluid line 116 to one lumen of dual lumen catheter 114, while used dialysis fluid is removed via the other lumen of dual lumen catheter 114 into used dialysis fluid line 118. Fresh dialysis fluid line 116 is separated from used dialysis fluid line 118 via sorbent cartridge 100.

In the illustrated embodiment, a single PD fluid pump 120 is provided along used dialysis fluid line 118 to pull used dialysis fluid from patient 112 via dual lumen catheter 114, and to push the used dialysis fluid through sorbent cartridge 100, and cleansed dialysis fluid from cartridge 100, through fresh dialysis fluid line 116, back to patient 112 via dual lumen catheter 114. A separate infusate pump 122 is used to meter a desired amount of PD electrolytes and make-up constituents into fresh dialysis fluid line 116 via a PD infusate container 124 and an infusate line 126 leading to the fresh dialysis fluid line.

A supply and UF line 128 leads from an initial fluid supply and UF container 130 to used dialysis fluid line 118 upstream of PD fluid pump 120. An initial supply of PD dialysis fluid is prepared in one embodiment by administering liquid or dried PD concentrate (e.g., dextrose/glucose and buffer) into container 130 and then delivering a specified amount of potable water, e.g., six to ten liters, into the container to mix (and dissolve if needed) the concentrate. PD fluid pump 120 is operated so as to pump the initial supply of dialysis fluid through sorbent cartridge 100 to purify the initial supply to an appropriate level before the initial supply reaches patient 112.

A weigh scale 132 is located beneath initial fluid supply and UF container 130 to proportion the PD concentrate and added potable water correctly and to allow a desired amount of UF to be removed from patient 112 over the course of treatment as described above for HD system 10. Weigh scale 132 as illustrated may be used additionally if needed (or a different scale may be used) with drain bag 136, so that with valves 140b and 140d closed and valve 140c open, PD fluid pump 120 can drive a desired amount of UF into the drain bag. The alternative UF control embodiments described above for HD system 10 may also be used with present PD system 110.

In the illustrated embodiment, system 110 also includes a drain line 134 leading to a drain container 136. Drain line 134 in one embodiment extends from used dialysis fluid line 118 at a location downstream of PD fluid pump 120. At the end of treatment, whatever dialysis fluid has not been pumped to UF container 130 is pumped instead to drain container 136. Drain line 134 leads alternatively to a house drain, such as a toilet or bathtub. Alternatively, all PD fluid and patient UF is delivered to drain bag 136 at the end of treatment.

PD system 110 in the illustrated embodiment includes multiple sensors, such as pressure sensors 138a and 138b located along fresh dialysis fluid line 116 and used dialysis fluid line 118, respectively, which are used to ensure that the negative pressure (pressure sensor 138b) and the positive pressure (pressure sensor 138a) applied to patient 112 via PD fluid pump 120 are within acceptable limits. An ammonia sensor 142 (and/or other physiological sensor) is located along fresh dialysis fluid line 116 and is used to ensure that regenerated dialysis fluid from sorbent cartridge 100 will be effective to remove toxins from patient 112 when returned to the patient.

Valve 140a is located along supply and UF line 128 to selectively allow or not allow initial fluid supply and UF container 130 to communicate fluidly with used dialysis fluid line 118. A valve 140b is located along infusate line 126 to selectively allow or not allow infusate container 124 to communicate fluidly with fresh dialysis fluid line 116. A valve 140c is located along drain line 134 to selectively allow or occlude flow through the drain line. Valves 140d and 140e are located in fresh dialysis fluid line 116 and used dialysis fluid lines 118, respectively, to selectively allow or occlude flow through those lines. As mentioned above, any valve discussed herein, including any of valves 140a to 140e may be an electrically actuated solenoid pinch valve that operates directly with the associated tube or line, or be a disposable-cassette based valve that is opened or closed pneumatically or electromechanically.

In the illustrated embodiment as indicated by the dashed electrical and/or signal lines, all dialysis fluid pumps and valves (such as valves 140a to 140e) are operated under control of a control unit 150, which also accepts inputs from each of the sensors described above operating with fresh dialysis fluid line 116 and used dialysis fluid lines 118, such as, pressure sensors 138a and 138b, conductivity sensors, air detection sensors, ammonia 142 and/or other chemical sensors.

An alternative PD system (not illustrated) uses a structure similar to HD system 10, which includes dialyzer 18. Here, blood circuit 20 is replaced with a patient PD fluid circuit. Dialysis fluid circuit 40 uses PD dialysis fluid to clean the patient PD fluid in circuit 20.

Sorbent cartridge 100 is located in PD dialysis fluid circuit 40 to cleanse waste and toxins from the PD dialysis fluid, which receives waste and toxins from the patient PD fluid in circuit 20 via dialyzer 18 through osmosis. All structure and functionality described above for HD system 10, such as for the pumps, valves and sensors, is applicable to the alternative dual loop CFPD system.

At the end of treatment using above-described HD system 10, sorbent cartridge 100 is removed from dialysis fluid circuit 40 and at least some of the layers of material within a sorbent column of the cartridge are cleaned and regenerated according to the embodiments described below.

Sorbent Material Refurbishing

With any of HD system 10, PD system 110 or the PD system using the structure of HD system 10 just described, it is contemplated to refurbished the sorbent materials in at least two different manners. In a first manner, patient 12, 112 or the caregiver collects used sorbent cartridges 100. The collected used cartridges are either picked up or delivered periodically to a facility where they are cleaned and regenerated in a batch manner along with used sorbent materials from other patients. Here, patient 12, 112 or the caregiver receives a delivery of fresh sorbent cartridges 100 periodically. In a second manner, at least a portion of used sorbent cartridges 100 are cleaned and regenerated onsite, either in a clinic or at home. In one example, any zirconium containing layers are cleaned and regenerated and then repacked into the sorbent column of cartridge 100 along with new single use layers. Single use layers in various embodiments include any one or more of a mechanical purification layer, a urease layer, an anion exchange layer and/or an activated carbon layer.

Batch Refurbishing

In the batch refurbishing primary embodiment, used sorbent materials from multiple sorbent cartridges 100 are combined and cleaned together. The sorbent cleaning process in one embodiment provides an adequate ammonium removal capacity of zirconium phosphate containing greater than 90% sodium or hydrogen exchange sites. The sorbent cleaning in various implementations involves the use of a disinfecting agent in combination with an acid, base or sodium salt treatment. The sorbent cleaning is applicable to sorbent cartridges 100 having different zirconium containing compartments provided in a serial (e.g., layered) or in parallel (e.g., used dialysis fluid flows through one or the other compartment).

It is contemplated to provide the batch sorbent refurbishing process in any one of a plurality of different implementations of the first primary embodiment. In each case, used zirconium containing sorbent materials from multiple sorbent cartridges 100 used by a single or multiple patients 12, 112 is collected at a refurbishing facility. The total batch to be refurbishing one procedure may be in the range of 10 lbs. to 1000 lbs.

In each of the batch refurbishing implementations discussed below, example reagents include:
  10 mM NH4Cl/PD solution (NH4Cl spiked PD Dianeal® solution),
  30 mM NH4Cl/PD solution (NH4Cl spiked PD Dianeal® solution),
  7 mM NH4Cl/PD solution (NH4Cl spiked PD Dianeal® solution),
  0.1N NaCl,
  0.1N HCL,
  0.1N NaOH, and
  0.5M NaHCO$_3$+0.1N NaOH The Dianeal® low calcium (2.5 mEq/L) peritoneal dialysis solution with 2.5% dextrose, catalog #5B9776. Each 100 ml contains
  2.5 g dextrose hydrous USP,
  538 mg sodium chloride USP,
  448 mg sodium lactate,
  18.3 mg calcium chloride USP,
  5.08 mg magnesium chloride USP, and
  pH 5.2
mEq/L:
  sodium—132,
  calcium—2.5,
  magnesium—0.5,
  chloride—95,
  lactate 40, and
  osmolarity 395 mOsmol/L In each of the batch refurbishing implementations discussed below, example sorbents include:

| Bottle | Sorbent | Lot |
|---|---|---|
| 1 | Terio ZP | 40051 commercial zirconium phospahte batch |
| 2 | JiangXi Zp | 20160113 commercial zirconium phospahte batch |
| 3 | Baxter ZP | NA commercial zirconium phospahte batch |
| 4 | REDY ZP | B-488 commercial zirconium phospahte batch |
| 5 | Terio ZP | 40054 commercial zirconium phospahte batch |
| 6 | Terio ZP | 40055 commercial zirconium phospahte batch |
| 7 | JiangXi Zp | 20160116 commercial zirconium phospahte batch |
| 8 | JiangXi Zp | 20160228 commercial zirconium phospahte batch |
| 9 | CarboChem | 100316-1 commercial zirconium phospahte batch |

In each of the batch refurbishing implementations discussed below, example equipment includes:
  three VWR tube rotator, 10136-084,
  one Rotoflex rotator, Argos, cat #R2000,
  50 ml Centrifuge tube, VWR,
  2 ml Micro tube, VWR, catalog #211-0092,
  universal fit screw caps with O-ring, VWR, catalog #211-0131, 211-0129,
  balance, L13831, L25833,
  pipette, RL-10532,
  stop watch, L31016,
  HPLC pump,
  bio-scale MT columns, bio-rad catalog number: 751-0081,
  1M NaCl, 0.5M NaHCO3, 2M NaHCO3, 1M CH3COONa,
  1M HCl, 0.5M HCl, and
  1M NaOH, 0.5M NaOH One example static sorbent sorption capacity test for the batch refurbishing embodiment includes:
  1. Dry zirconium phosphate (ZP) is contacted with PD low calcium dialysate solution at the ration of 7 g sorbent in 1 L PD solution containing 10 mM of ammonium chloride.
  2. The suspension is mixed using stirring bar at room temperature for 1 hr.
  3. 1.0 ml control samples were taken from the 10 mM NH4Cl/PD.
  4. Three test samples were collected from supernatant at time=1 hour.

5. The control and test samples were sent for chemical analysis to measure the concentration of $NH_4^+$, BUN, Bicarbonate, $Na^+$, phosphorus, $Ca^{2+}$ and $Mg^{2+}$, $K^+$ and pH.
6. $NH_4^+$ sorption capacity in zirconium phosphate is calculated.

Example data analysis for a static sorbent sorption capacity test for the batch refurbishing embodiment includes:

Static Sorption Test $NH_4^+$ adsorption is obtained by equation 1:

$$q = \frac{(C_i - C_e) \cdot L}{ZP} \quad \text{Equation 1}$$

where:
q: adsorbed $NH_4^+$ (mmol $NH_4^+$/g ZP),
$C_i$: initial concentration of $NH_4^+$ in dialysate solution (mmol/L),
$C_e$: concentration of $NH_4^+$ at equilibrium (mmol/L),
L: volume of test solution, and
ZP: dosage of ZP added to the bottle (grams)

Dynamic Sorption Test $NH_4^+$ adsorption is obtained by equation 2:

$$q = \frac{[NH4+] \times Q \times BT \times 0.001}{ZP} \quad \text{Equation 2}$$

where:
q: adsorbed NH4+ (mmol $NH_4^+$/g ZP),
$[NH_4^+]$: feed concentration of $NH_4^+$ in dialysate solution (mmol/L),
Q: flow rate (ml/min),
BT: $NH_4^+$ break through time (min), and
ZP: dosage of ZP added to the bottle (grams)

Figure 3:
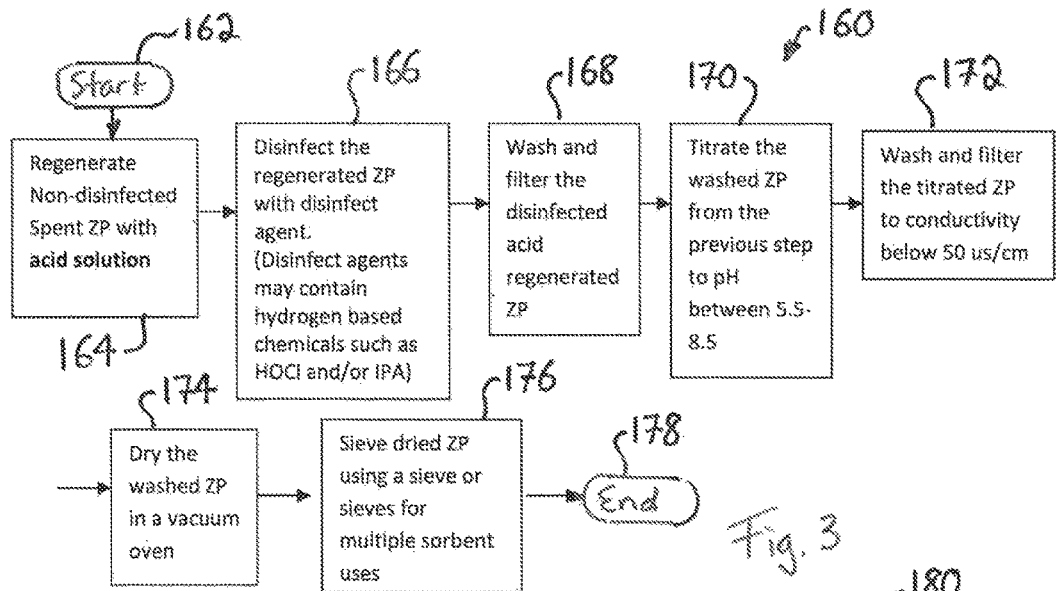
FIG. 3 is a schematic diagram of a first batch sorbent implementation of the present disclosure.

Referring now to FIG. 3, a first batch sorbent refurbishing implementation is illustrated by method 160. At oval 162, method 160 begins. At block 164, non-disinfected zirconium phosphate ("ZP") is removed and collected from the relevant casings in the columns of each of a plurality of used sorbent cartridges 100 returned to the sorbent refurbishing facility. The collected and combined non-disinfected ZP is regenerated using an acid solution.

At block 166, the regenerated ZP is disinfected using a disinfecting agent. The disinfecting agent in various examples includes any one or more of various types of chemicals. One is a sodium based chemical such as NaOCl in isopropyl alcohol ("IPA"). The other is hydrogen based chemical such as HOCl in IPA. A third includes IPA as the primary disinfecting agent.

At block 168, the disinfected and acid regenerated ZP is washed and filtered. Washing and filtering is performed in one example by flowing water through the disinfected and acid refurbished ZP, rinsing any residue from the disinfection and the acid regeneration.

At block 170, the washed ZP is titrated to a desired pH, for example, to a pH between and including 5.5 to 8.5. Titration may be performed using an analyte, an indicator and a pH meter. The titration is performed to the entire batch in one embodiment. The washed ZP is stirred in aqueous suspension at room temperature and the pH is continuously monitored. The pH of the suspension is adjusted by adding small aliquotes of diluted basic solution (e.g. 0.1 N NaOH and/or 0.5 M NaHCO3) If the pH rises above the desired range, small aliquotes of diluted acid solution (e.g. 0.1 N HCl) can be added.

At block 172, the titrated ZP is washed and filtered to a conductivity below 50 µS/cm. Washing and filtering is performed again in one example using water, which subsequent to washing and filtering the ZP is flowed, e.g., pumped, past a temperature-compensated conductivity probe that reads out to a conductivity meter. Once the meter reads below 50 µS/cm, the washing and filtering at block 172 may be stopped.

At block 174, the washed ZP is dried, e.g., in a vacuum oven at 120° C. or greater for a duration known to completely dry the washed mass of ZP.

At block 176, the dried ZP is sieved using one or more sieves for one or more sorbent uses. Sieving produces ZP granules having at least a minimum desired smallest diameter needed for the intended use. The sieved ZP granules are then placed back into a casing, which may have also been disinfected. The casing is placed in a desired order within a column of a refurbished sorbent cartridge 100, which is now ready to be used again in treatment, and may be shipped to a patient's home or clinic.

At oval 178, method 160 ends.

Figure 4:
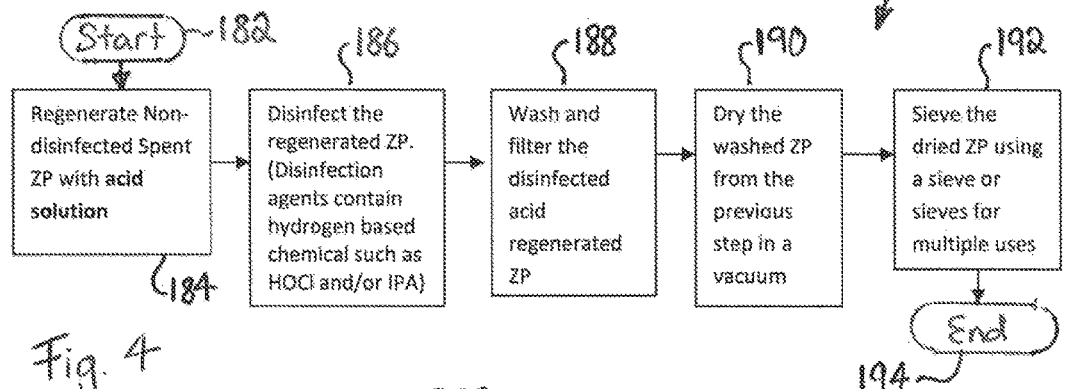
FIG. 4 is a schematic diagram of a second batch sorbent refurbishing implementation of the present disclosure.

Referring now to FIG. 4, a second batch sorbent refurbishing implementation is illustrated by method 180. In method 180, the titration at block 170 and the second washing procedure at block 172 of method 170 are removed. At oval 182, method 180 begins.

At block 184, non-disinfected zirconium phosphate ("ZP") is removed and collected from the relevant casings in the columns of each of a plurality of used sorbent cartridges 100 returned to the sorbent refurbishing facility. The collected and combined non-disinfected ZP is regenerated using an acid solution.

At block 186, the regenerated ZP is disinfected using a disinfecting agent.

The disinfecting agent includes any one or more of (i) a sodium based chemical such as NaOCl in isopropyl alcohol ("IPA"), (ii) a hydrogen based chemical such as HOCl in IPA or (iii) IPA as the primary disinfectant.

At block 188, the disinfected and acid regenerated ZP is washed and filtered, which in an example is performed by flowing water through the disinfected and acid regenerated ZP, rinsing any residue from the disinfection and the acid regeneration.

At block 190, the washed ZP is dried, e.g., in a vacuum oven at 120° C. or greater for a duration known to completely dry the washed mass of ZP.

At block 192, the dried ZP is sieved using one or more sieves for one or more sorbent uses. The sieved ZP granules are then placed back into a casing, which may have also been disinfected. The casing is placed in a desired order within a column of a refurbished sorbent cartridge 100, which is now ready to be used again in treatment, and may be shipped to a patient's home or clinic.

At oval 194, method 180 ends.

Figure 5:
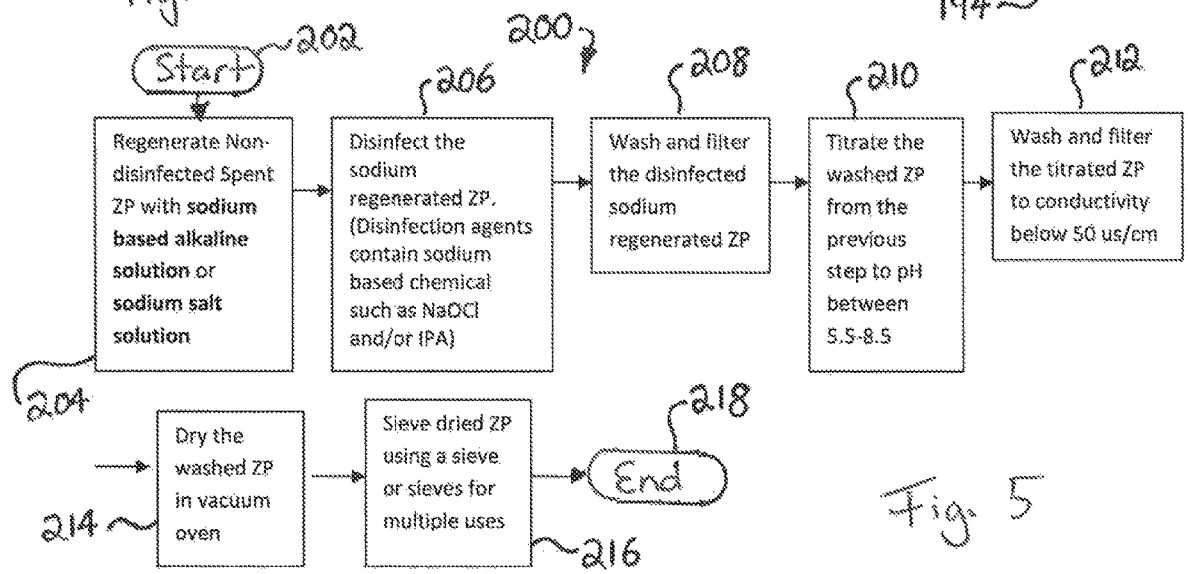
FIG. 5 is a schematic diagram of a third batch sorbent refurbishing implementation of the present disclosure.

Referring now to FIG. 5, a third batch sorbent refurbishing implementation is illustrated by method 200. In method 200, the acid solution of method 160 is replaced with a sodium based alkaline solution or a sodium salt solution. At oval 202, method 200 begins.

At block 204, non-disinfected zirconium phosphate ("ZP") is removed and collected from the relevant casings in the columns of each of a plurality of used sorbent cartridges 100 returned to the sorbent refurbishing facility. The collected and combined non-disinfected ZP is regenerated using a sodium based alkaline solution or a sodium salt solution.

At block 206, the regenerated ZP is disinfected using a disinfecting agent. The disinfecting agent includes any one or more of (i) a sodium based chemical such as NaOCl in isopropyl alcohol ("IPA"), (ii) a hydrogen based chemical such as HOCl in IPA, or (iii) IPA as the primary disinfecting agent.

At block 208, the disinfected and sodium regenerated ZP is washed and filtered, which in an example is performed by flowing water through the disinfected and sodium regenerated ZP, rinsing any residue from the disinfection and the acid regeneration.

At block 210, the washed ZP is titrated to a desired pH, for example, to a pH between and including 5.5 to 8.5. Titration may be performed using an analyte, an indicator and a pH meter. The titration is performed to the entire batch in one embodiment. The washed ZP is stirred in aqueous suspension at room temperature and the pH is continuously monitored.

The pH of the suspension is adjusted by adding small aliquotes of diluted basic solution (e.g. 0.1 N NaOH and/or 0.5 M $NaHCO_3$) If the pH rises above the desired range, small aliquotes of diluted acid solution (e.g. 0.1 N HCl) can be added.

At block 212, the titrated ZP is washed and filtered to a conductivity below 50 μS/cm. Washing and filtering is performed again in one example using water, which subsequent to washing and filtering the ZP is flowed, e.g., pumped, past a temperature-compensated conductivity probe that reads out to a conductivity meter. Once the meter reads below 50 μS/cm, the washing and filtering at block 172 may be stopped.

At block 214, the washed ZP is dried, e.g., in a vacuum oven at 120° C. or greater for a duration known to completely dry the washed mass of ZP.

At block 216, the dried ZP is sieved using one or more sieves for one or more sorbent uses. The sieved ZP granules are then placed back into a casing, which may have also been disinfected. The casing is placed in a desired order within a column of a refurbished sorbent cartridge 100, which is now ready to be used again in treatment, and may be shipped to a patient's home or clinic.

At oval 218, method 200 ends.

Figure 6:
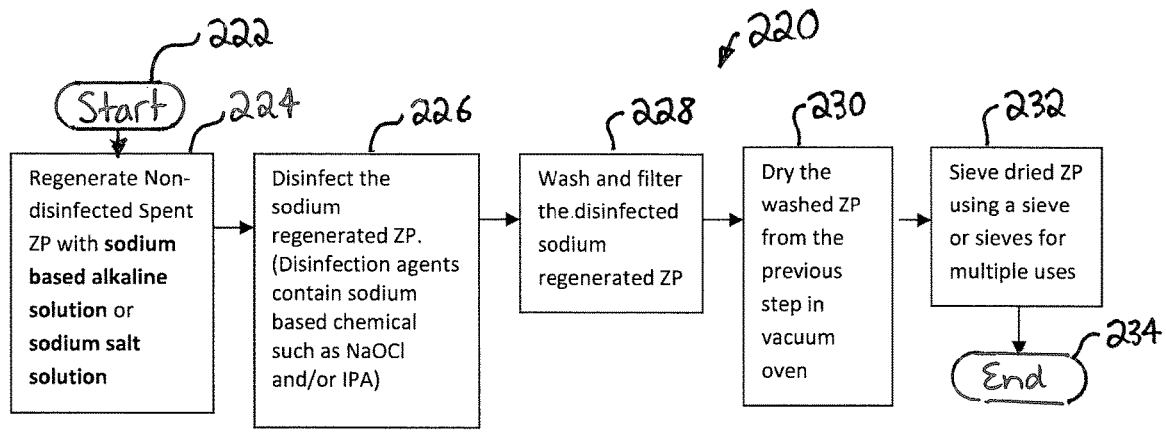
FIG. 6 is a schematic diagram of a fourth batch sorbent refurbishing implementation of the present disclosure.

Referring now to FIG. 6, a fourth batch sorbent refurbishing implementation is illustrated by method 220. In method 220, the acid solution of method 180 is replaced with a sodium based alkaline solution or a sodium salt solution. At oval 222, method 220 begins.

At block 224, non-disinfected zirconium phosphate ("ZP") is removed and collected from the relevant casings in the columns of each of a plurality of used sorbent cartridges 100 returned to the sorbent refurbishing facility. The collected and combined non-disinfected ZP is regenerated using a sodium based alkaline solution or a sodium salt solution.

At block 226, the regenerated ZP is disinfected using a disinfecting agent.

The disinfecting agent includes any one or both of (i) a sodium based chemical such as NaOCl in isopropyl alcohol ("IPA"), (ii) a hydrogen based chemical such as HOCl in IPA, or (iii) IPA as the primary disinfecting agent.

At block 228, the disinfected and sodium regenerated ZP is washed and filtered, which in an example is performed by flowing water through the disinfected and sodium regenerated ZP, rinsing any residue from the disinfection and the sodium regeneration.

At block 230, the washed ZP is dried, e.g., in a vacuum oven at 120° C. or greater for a duration known to completely dry the washed mass of ZP.

At block 232, the dried ZP is sieved using one or more sieves for one or more sorbent uses. The sieved ZP granules are then placed back into a casing, which may have also been disinfected. The casing is placed in a desired order within a column of a refurbished sorbent cartridge 100, which is now ready to be used again in treatment, and may be shipped to a patient's home or clinic.

At oval 234, method 220 ends.

Figure 7:
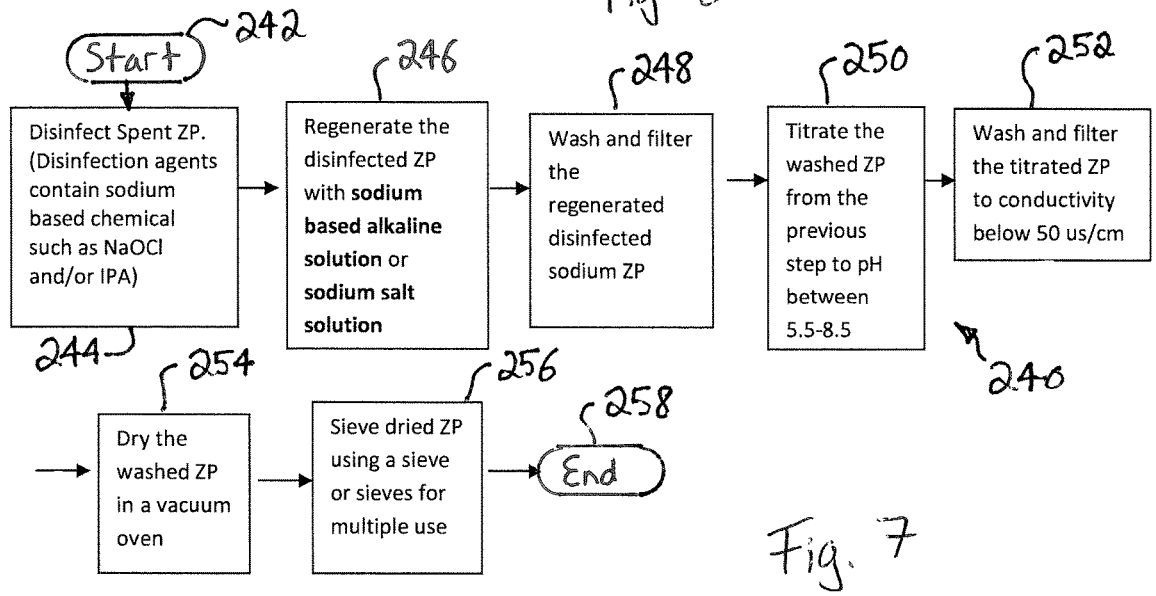
FIG. 7 is a schematic diagram of a fifth batch sorbent refurbishing implementation of the present disclosure.

Referring now to FIG. 7, a fifth batch sorbent refurbishing implementation is illustrated by method 240. In method 240, the regenerating and disinfecting procedures at blocks 204 and 206 of method 200 are reversed. At oval 242, method 240 begins.

At block 244, non-regenerated zirconium phosphate ("ZP") is removed and collected from the relevant casings in the columns of each of a plurality of used sorbent cartridges 100 returned to the sorbent refurbishing facility. The collected and combined non-regenerated ZP is disinfected using a disinfecting agent. The disinfecting agent includes any one or both of (i) a sodium based chemical such as NaOCl in isopropyl alcohol ("IPA"), (ii) a hydrogen based chemical such as HOCl in IPA, or (iii) IPA as the primary disinfecting agent.

At block 246, the disinfected ZP is regenerated using a sodium based alkaline solution or a sodium salt solution.

At block 248, the disinfected and sodium regenerated ZP is washed and filtered, which in an example is performed by flowing water through the disinfected and sodium regenerated ZP, rinsing any residue from the disinfection and the sodium regeneration.

At block 250, the washed ZP is titrated to a desired pH, for example, to a pH between and including 5.5 to 8.5. Titration may be performed using an analyte, an indicator and a pH meter. The titration is performed to the entire batch in one embodiment. The washed ZP is stirred in aqueous suspension at room temperature and the pH is continuously monitored. The pH of the suspension is adjusted by adding small aliquotes of diluted basic solution (e.g. 0.1 N NaOH and/or 0.5 M $NaHCO_3$) If the pH rises above the desired range, small aliquotes of diluted acid solution (e.g. 0.1 N HCl) can be added.

At block 252, the titrated ZP is washed and filtered to a conductivity below 50 μS/cm. Washing and filtering is performed again in one example using water, which subsequent to washing and filtering the ZP is flowed, e.g., pumped, past a temperature-compensated conductivity probe that reads out to a conductivity meter. Once the meter reads below 50 μS/cm, the washing and filtering at block 172 may be stopped.

At block 254, the washed ZP is dried, e.g., in a vacuum oven at 120° C. or greater for a duration known to completely dry the washed mass of ZP.

At block 256, the dried ZP is sieved using one or more sieves for one or more sorbent uses. The sieved ZP granules are then placed back into a casing, which may have also been disinfected. The casing is placed in a desired order within a column of a refurbished cartridge 100, which is now ready to be used again in treatment, and may be shipped to a patient's home or clinic.

At oval 258, method 240 ends.

Figure 8:
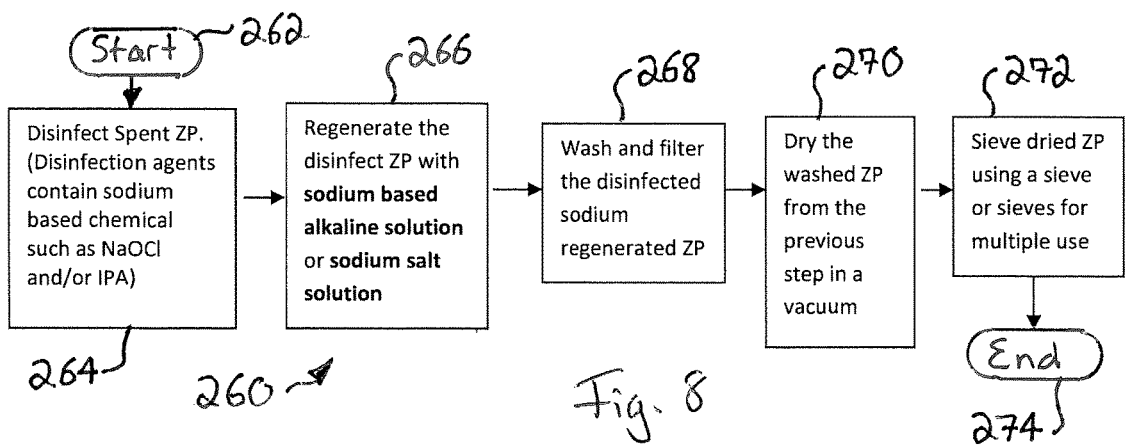
FIG. 8 is a schematic diagram of a sixth batch sorbent refurbishing implementation of the present disclosure.

Referring now to FIG. 8, a sixth batch sorbent refurbishing implementation is illustrated by method 260. In method

260, the regenerating and disinfecting procedures at blocks 224 and 226 of method 220 are reversed. At oval 262, method 260 begins.

At block 264, non-regenerated zirconium phosphate ("ZP") is removed and collected from the relevant casings in the columns of each of a plurality of used sorbent cartridges 100 returned to the sorbent refurbishing facility. The collected and combined non-regenerated ZP is disinfected using a disinfecting agent. The disinfecting agent includes any one or both of (i) a sodium based chemical such as NaOCl in isopropyl alcohol ("IPA"), (ii) a hydrogen based chemical such as HOCl in IPA, or (iii) IPA as the primary disinfecting agent.

At block 266, the disinfected ZP is regenerated using a sodium based alkaline solution or a sodium salt solution.

At block 268, the disinfected and sodium regenerated ZP is washed and filtered, which in an example is performed by flowing water through the disinfected and sodium regenerated ZP, rinsing any residue from the disinfection and the sodium regeneration.

At block 270, the washed ZP is dried, e.g., in a vacuum oven at 120° C. or greater for a duration known to completely dry the washed mass of ZP.

At block 272, the dried ZP is sieved using one or more sieves for one or more sorbent uses. The sieved ZP granules are then placed back into a casing, which may have also been disinfected. The casing is placed in a desired order within a column of a refurbished sorbent cartridge 100, which is now ready to be used again in treatment, and may be shipped to a patient's home or clinic.

At oval 274, method 260 ends.

In any of the above implementations for refurbishing ZP for reuse is applicable to other zirconium containing materials, such as zirconium oxide ("ZO") and to different types of ZP, such as H$^+$ZP and Na$^+$ZP. The layers form a refurbished sorbent cartridge 100 that is deliverable to the patient along with other refurbished cartridges 100 to be used over multiple treatments.

Moreover, the ZP made ready for reuse via any of the implementations above may be placed within the column of sorbent cartridge 100 in a serial or parallel fashion with other zirconium containing materials, and with reused and/or new non-zirconium layers, such as mechanical filtration, urease, anion and activated carbon exchange layers. For example, ZP from any of methods 160, 200 or 240 forms an Na/H refurbished sorbent, which may be packed in a casing spanning the entire diameter of the column of sorbent cartridge 100 for reuse.

In any of the batch implementations, the acid solution may be HCl, H$_2$SO$_4$, H$_3$PO$_4$, HNO$_3$ or acetic acid, while the sodium based alkaline solution or a sodium salt solution may be NaOH, NaHCO$_3$, Na$_2$CO$_3$ or NaCl.

Figure 9:
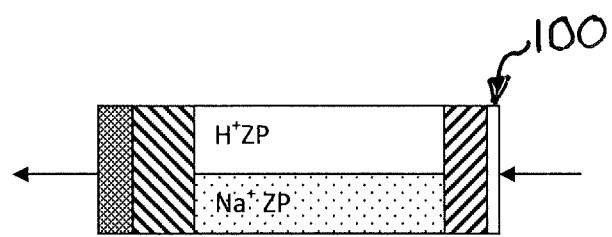
FIG. 9 is a schematic diagram of an example parallel path sorbent cartridge formed via certain implementations of the batch refurbishing of the present disclosure.

ZP from method 180 contains greater than 90% hydrogen ion exchange sites. The ZP from method 180 may be packed in an H$^+$ZP casing for a parallel cartridge 100 as shown in FIG. 9. ZP from methods 220 and 260 contains greater than 90% sodium ion exchange sites. The ZP from methods 220 and 260 may be packed in Na$^+$ZP column for parallel cartridge as shown in FIG. 9.

Onsite Refurbishing

In a second primary embodiment, sorbent material refurbishing is performed in an onsite operation in which at least the zirconium containing materials (e.g., ZO, H$^+$ZP and Na$^+$ZP) are conditioned for reuse. As with the previous primary embodiment, the sorbent refurbishing process of the second primary embodiment may provide an adequate ammonium removal capacity of zirconium phosphate containing greater than 90% sodium or hydrogen exchange sites. The sorbent refurbishing in various implementations again involves the use of a disinfecting agent in combination with an acid, base or sodium salt treatment. The sorbent refurbishing is applicable to sorbent cartridges 100 having different zirconium containing compartments provided in a serial (e.g., layered) or in parallel (e.g., used dialysis fluid flows through one or the other compartment).

A primary difference between the first and second primary embodiments is that in the batch process, the sorbent materials are removed from their layering casing, so that the materials from multiple sorbent cartridges 100 may be mixed together and cleaned at once.

In the onsite embodiment, on the other hand, the sorbent materials are left to reside within their casings, for ease of handling and so that the patient or caregiver does not have to handle the sorbent materials directly.

In each of the onsite refurbishing implementations discussed below, example reagents include:
7 mM NH4Cl/PD solution (NH4Cl spiked PD Dianeal® solution),
0.1N NaCl,
0.1N HCL,
0.1N NaOH, and
0.5M NaHCO$_3$+0.1N NaOH The Dianeal® low calcium (2.5 mEq/L) peritoneal dialysis solution with 2.5% dextrose, catalog #5B9776. Each 100 ml contains:
2.5 g dextrose hydrous USP,
538 mg sodium chloride USP,
448 mg sodium lactate,
18.3 mg calcium chloride USP,
5.08 mg magnesium chloride USP, and
pH 5.2 mEq/L:
sodium 132,
calcium 2.5,
magnesium 0.5,
chloride 95,
lactate 40, and
osmolarity 395 mOsmol/L In each of the onsite refurbishing implementations discussed below, example sorbents include:

| Bottle | Sorbent | lot | |
|---|---|---|---|
| 1 | Terio ZP | 40051 | commercial zirconium phospahte batch |
| 2 | JiangXi Zp | 20160113 | commercial zirconium phospahte batch |
| 3 | Baxter ZP | NA | commercial zirconium phospahte batch |
| 4 | REDY ZP | B-488 | commercial zirconium phospahte batch |
| 5 | Terio ZP | 40054 | commercial zirconium phospahte batch |
| 6 | Terio ZP | 40055 | commercial zirconium phospahte batch |
| 7 | JiangXi Zp | 20160116 | commercial zirconium phospahte batch |
| 8 | JiangXi Zp | 20160228 | commercial zirconium phospahte batch |
| 9 | CarboChem | 100316-1 | commercial zirconium phospahte batch |

In each of the onsite refurbishing implementations discussed below, example equipment includes:
2 ml Micro tube, VWR, catalog #211-0092,
universal fit screw caps with O-ring, VWR, catalog #211-0131, 211-0129,
balance, L13831, L25833,
pipette, RL-10532,
stop watch, L31016,
HPLC pump, bio-Scale MT columns, Bio-Rad catalog number:751-0081, 1M NaCl, 0.5M NaHCO3, 2M NaHCO3, 1M CH3COONa, 0.1 N HCl, and 0.1N NaOH One example sorbent sorption capacity test for the onsite refurbishing embodiment uses a parallel chamber sorbent cartridge 100 illustrated in FIG. 10. Here, sorbent cartridge 100 includes a cartridge housing 80 forming the column of the cartridge. Housing 80 holds an inlet activated carbon and filter casing 96 and an outlet activated carbon and filter casing 98. A urease casing 102 is located just downstream from inlet activated carbon and filter casing 96. An anion exchange resin casing 104 is located just upstream from outlet activated carbon and filter casing 98. In between urease casing 102 and anion exchange resin casing 104 are two parallel ZP casings, namely, an $H^+ZP$ casing 106 and an $Na^+ZP$ casing 108.

It should be appreciated that $H^+ZP$ casing 106 and an $Na^+ZP$ casing 108 may be moved collectively to a different order, e.g., downstream of anion exchange resin casing 104 or upstream of urease casing 102. It should also be appreciated that parallel ZP casings do not have to be provided and that a single $H^+ZP$ casing 106 or $Na^+ZP$ casing 108 sized to span the entire diameter of housing 80 may be provided instead. The analysis below applies equally to a sorbent cartridge 100 having only one of $H^+ZP$ casing 106 or $Na^+ZP$ casing 108, or a sorbent cartridge 100 having serially juxtaposed $H^+ZP$ and $Na^+ZP$ casings 106 and 108.

Figure 10:
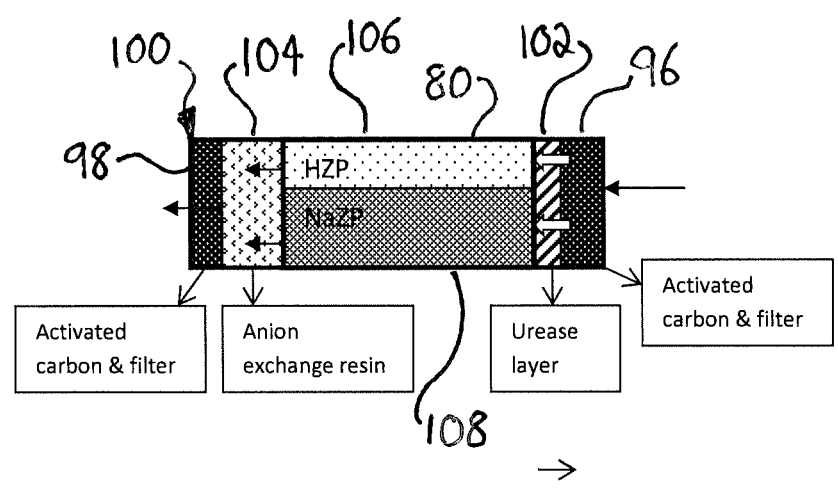
FIG. 10 is a schematic diagram of an example parallel path sorbent cartridge formed via certain implementations of the onsite refurbishing of the present disclosure.

One example sorption capacity test for sorbent cartridge 100 illustrated in FIG. 10 includes:

1. 7 mM $NH_4Cl$/PD solution is passed through the ZP column/cartridge at 1.5 ml/min flow rate.
2. 1 ml eluent samples are collected at different time points and are sent for chemical analysis to measure the concentration of $NH_4^+$, BUN, Bicarb, $Na^+$, P, $Ca^{2+}$ and $Mg^{2+}$, $K^+$ and pH.
3. Ammonia break through point is determined at the time point where $[NH_3]$ concentration of eluent sample reaches 1 mmol/L. $NH_3$ sorption capacity is calculated according to equation 3 below.

One example column regeneration procedure for sorbent cartridge 100 illustrated in FIG. 10 includes:

1. Rinse parallel columns, e.g., pump water through both columns to rinse the excess sugar, debris and ion.
2. Regenerate and disinfect both columns, e.g., reverse flow path for regeneration.
3. The regeneration and disinfection solution for $H^+ZP$ contains acid.
4. The regeneration and disinfection solution for $Na^+ZP$ contains sodium.

Example data analysis for a static sorbent sorption capacity test for the onsite refurbishing embodiment includes:

Dynamic Sorption Test $NH_4^+$ adsorption is obtained by equation 3:

$$q = \frac{[NH4+] \times Q \times BT \times 0.001}{ZP} \quad \text{Equation 3}$$

where:

q: Adsorbed $NH_3$ (mmol $NH_4^+$/g ZP), $[NH_4^+]$: feed concentration of $NH_4^+$ in dialysate solution (mmol/L), Q: flow rate (ml/min), BT: $NH_4^+$ break through time (min), and ZP: dosage of ZP added to the bottle (grams)

Figure 11:
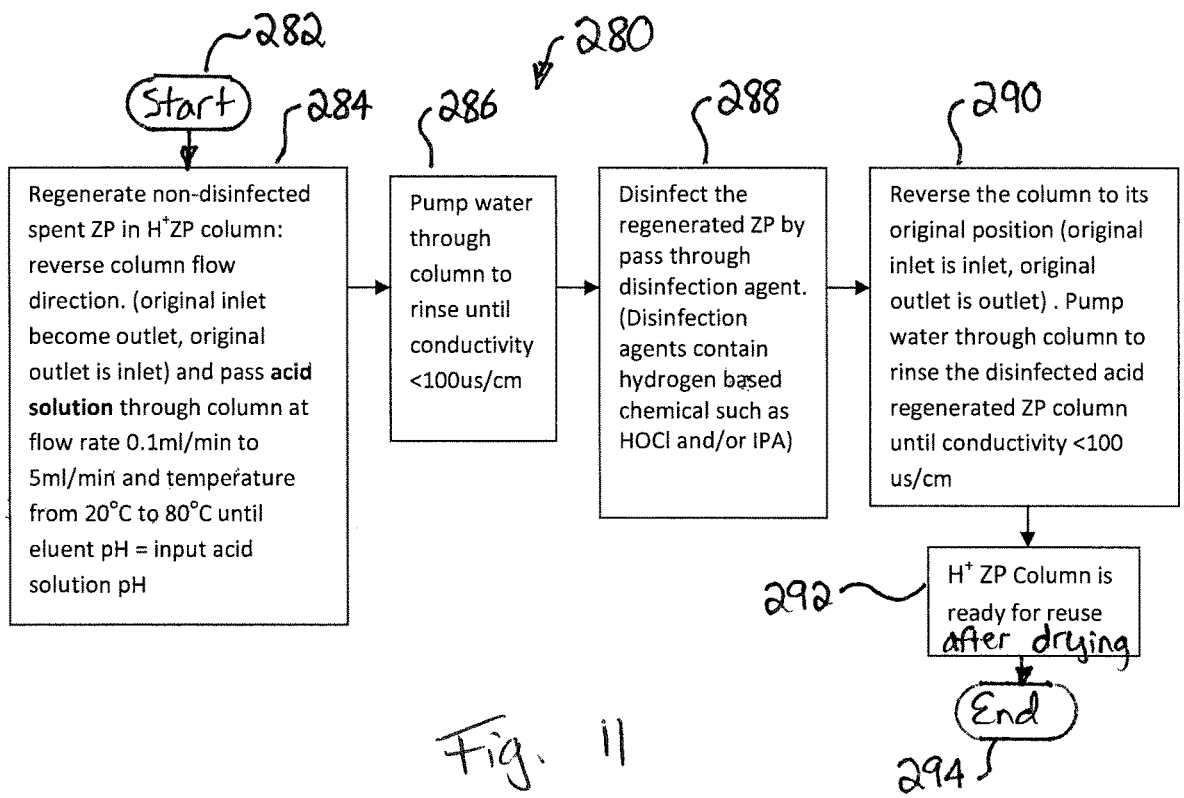
FIG. 11 is a schematic diagram of an onsite $H^+ZP$ sorbent refurbishing implementation of the present disclosure.

Referring now to FIG. 11, one onsite sorbent refurbishing implementation for $H^+ZP$ casing 106 is illustrated by method 280. At oval 282, method 280 begins. At block 284, non-disinfected $H^+ZP$ is regenerated within casing 106 in a reverse flow direction to operational flow through sorbent cartridge 100. Here, an inlet of casing 106 during treatment becomes instead the outlet of casing 106 outlet during regeneration and vice versa. An acid solution is flowed, e.g., pumped, through casing 106 at a flow rate of for example 0.1 ml/min to 5 ml/min and at a temperature from about 20° C. to about 80° C. The acid wash is performed in one example until the pH of the eluent (acid that has contacted $H^+ZP$) equals or almost equals the pH of the incoming acid solution.

At block 286, water is rinsed (e.g., pumped) through the regenerated $H^+ZP$ within casing 106 (e.g., in the reverse flow direction) until a conductivity of the effluent (water used to wash regenerated $H^+ZP$) reaches a conductivity of 100 µS/cm or less.

At block 288, the regenerated and rinsed $H^+ZP$ is disinfected via a disinfecting agent, which in various examples includes a hydrogen based chemical, such as HOCl in IPA, flowed, e.g., pumped, through the $H^+ZP$ casing 106 (e.g., in the reverse flow direction).

At block 290, flow is reversed and water is rinsed, e.g., pumped through the regenerated and disinfected $H^+ZP$ casing 106 in the normal treatment flow direction until conductivity of the eluent (water used to wash regenerated and disinfected $H^+ZP$) reaches a conductivity of 100 µS/cm or less.

At block 292, $H^+ZP$ casing 106 is dried and is ready to be reintroduced into sorbent cartridge 100 and reused. At oval 294, method 280 ends.

Figure 12:
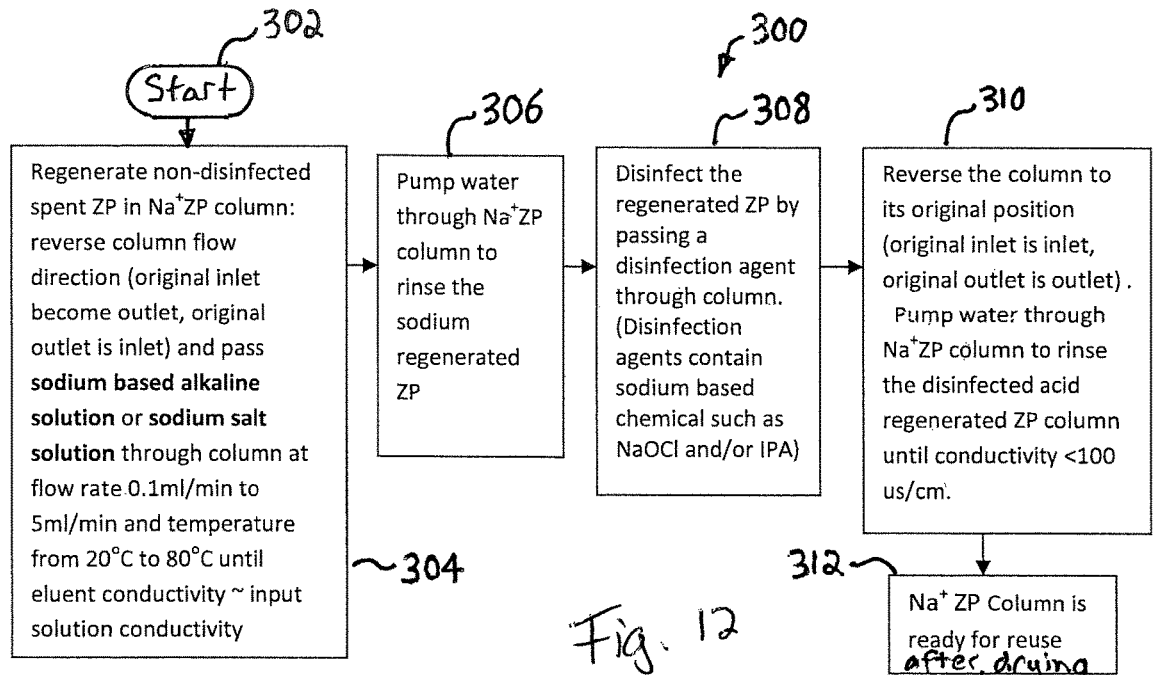
FIG. 12 is a schematic diagram of a first onsite $Na^+ZP$ sorbent refurbishing implementation of the present disclosure.

Referring now to FIG. 12, one onsite sorbent refurbishing implementation for $Na^+ZP$ casing 108 is illustrated by method 300. At oval 302, method 300 begins. At block 304, non-disinfected $Na^+ZP$ is regenerated within its casing in a reverse-to-operational flow direction, such that an inlet of $Na^+ZP$ casing 108 during treatment becomes the outlet of $Na^+ZP$ casing 108 during regeneration and vice versa. A sodium based alkaline solution or a sodium salt solution is flowed, e.g., pumped, through $Na^+ZP$ casing 108 at a flow rate of for example 0.1 ml/min to 5 ml/min, and at a temperature from about 20° C. to about 80° C. The sodium regeneration may be performed until the conductivity of the eluent (sodium solution that has contacted $Na^+ZP$) equals or almost equals the conductivity of the incoming sodium solution.

At block 306, water is rinsed through the regenerated $Na^+ZP$ within its casing 108 (e.g., in the reverse flow direction,) for a determined time knowing that the conductivity has already been controlled at block 384.

At block 308, the regenerated and rinsed $Na^+ZP$ is disinfected via a disinfecting agent, which in various examples includes a sodium based chemical, such as NaOCl in IPA, flowed, e.g., pumped, through the $Na^+ZP$ casing (e.g., in the reverse flow direction).

At block 310, flow is reversed and water is rinsed, e.g., pumped, through the regenerated and disinfected $Na^+ZP$ within its casing 108 in the normal treatment flow direction until conductivity of the eluent (water used to wash regenerated and disinfected $Na^+ZP$) reaches a conductivity of 100 µS/cm or less.

At block 312, Na⁺ZP casing 108 is dried and is ready to be reintroduced into sorbent cartridge 100 and reused. At oval 314, method 300 ends.

Figure 13:
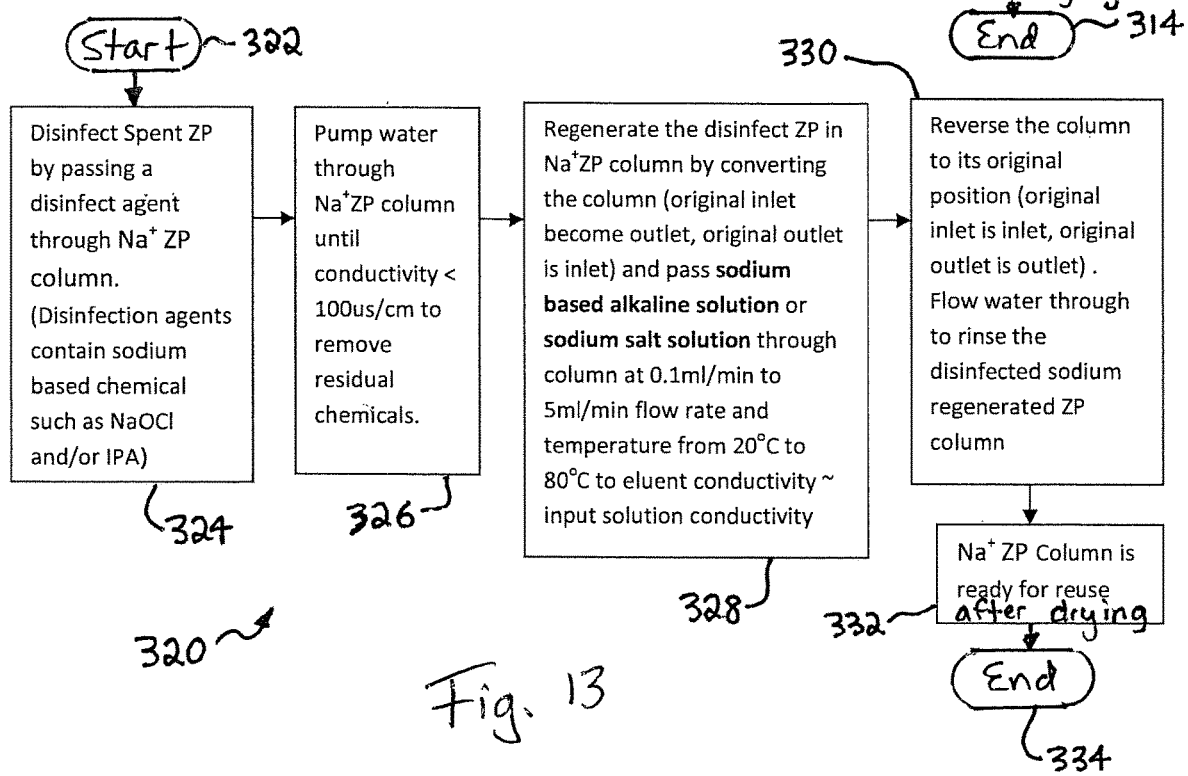
FIG. 13 is a schematic diagram of a second onsite $Na^+ZP$ sorbent refurbishing of the present disclosure.

Referring now to FIG. 13, a second onsite sorbent refurbishing implementation for Na⁺ZP casing 108 is illustrated by method 320. Here, the regeneration and disinfection procedures of method 300 are reversed. At oval 322, method 300 begins. At block 324, used and non-regenerated Na⁺ZP is disinfected within its casing 108 in a normal treatment or reverse flow direction, e.g., via pumping, using a disinfecting agent that may contain a sodium based chemical such as NaOCl in IPA.

At block 326, water is rinsed, e.g., pumped, through the disinfected Na⁺ZP within its casing 108, in a normal treatment or reverse flow direction, to remove residual disinfecting chemicals until the conductivity of the eluent (water used to wash disinfected Na⁺ZP) reaches a conductivity of 100 µS/cm or less.

At block 328, disinfected Na⁺ZP is regenerated within its casing 108 in the reverse flow direction, such that the inlet of casing 108 during treatment becomes the outlet of casing 108 during regeneration and vice versa. A sodium based alkaline solution or a sodium salt solution is flowed, e.g., pumped, through casing 108 at a flow rate of for example 0.1 ml/min to 5 ml/min and at a temperature from about 20° C. to about 80° C. Regeneration is performed in one embodiment until the conductivity of the eluent (sodium solution that has contacted Na⁺ZP) equals or almost equals the conductivity of the incoming sodium solution.

At block 330, flow is reversed and water is rinsed, e.g., pumped, through the disinfected and regenerated Na⁺ZP within its casing 108 in the normal treatment flow direction, e.g., for a determined amount of time (knowing that conductivity has already been controlled at blocks 326 and 328.

At block 332, Na⁺ZP casing 108 is dried and is ready to be reintroduced into sorbent cartridge 100 and reused. At oval 334, method 300 ends.

Once any or all of the H⁺ZP and Na⁺ZP casings 106 and 108 are refurbished or conditioned for reuse, patient 12, 112 or caregiver inserts the reusable casings into cartridge housing 80 of sorbent cartridge 100 along with any additional casings, e.g., mechanical filtration casing, urease casing, anion exchange casing, and/or activated carbon casing(s), which may themselves have been conditioned for reuse or opened from a sterile package as a new casing. Patient 12, 112 or caregiver inserts all casings in a proper order and orientation, which may be aided by markings provided on the outside of sorbent cartridge. Alternatively or additionally, housing 80 of cartridge 100 and the casings may be somewhat conical in shape so that the casings only fit snugly within the cartridge when stacked in the proper order and orientation.

In any of the onsite implementations, the acid solution may be HCl, $H_2SO_4$, $H_3PO_4$, $HNO_3$ or acetic acid, while the sodium based alkaline solution or a sodium salt solution may be NaOH, $NaHCO_3$, $Na_2CO_3$ or NaCl.

Figure 14:
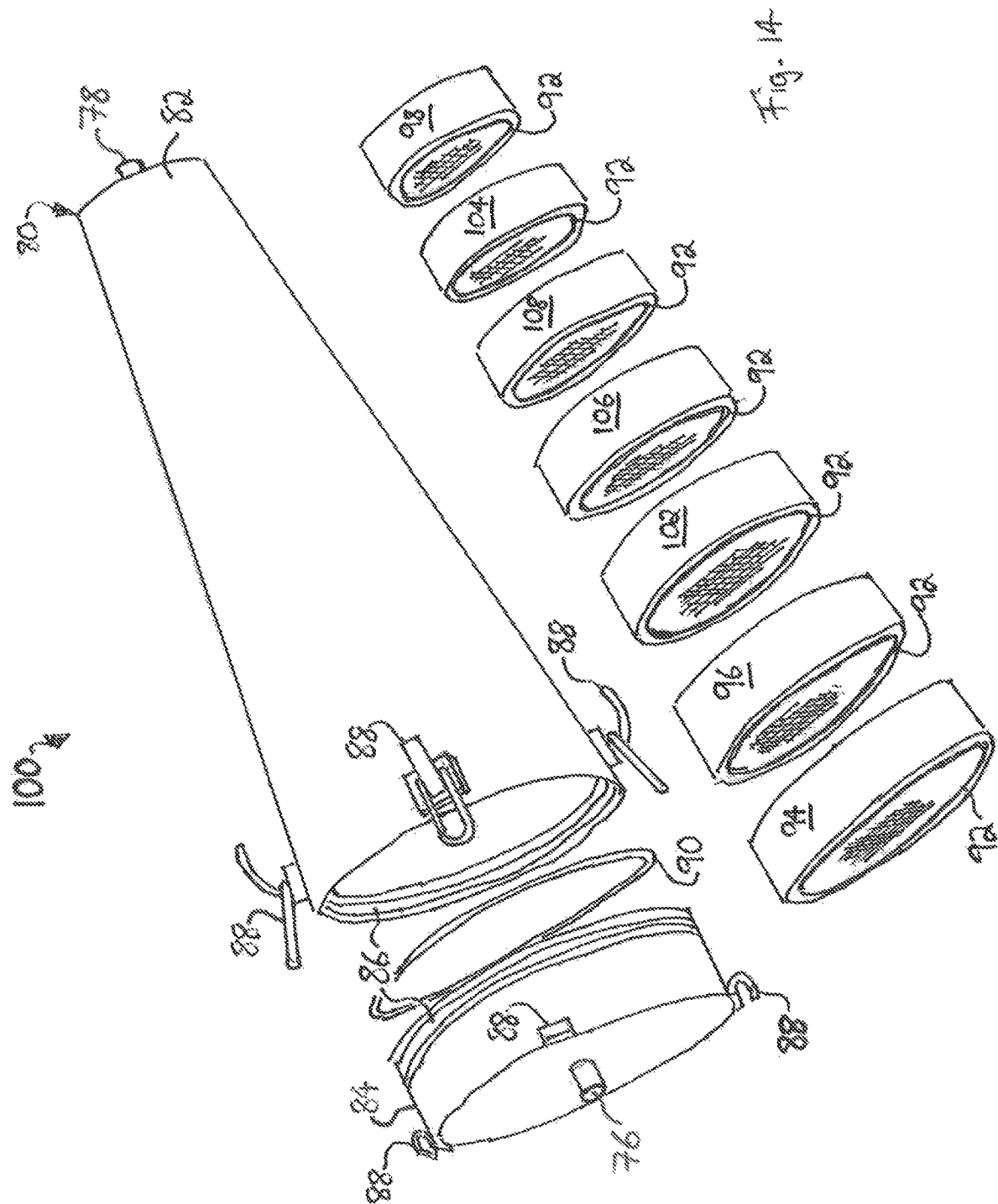
FIG. 14 is an exploded perspective view of one embodiment of a sorbent cartridge that may be used with the onsite sorbent refurbishing of the present disclosure.

Referring now to FIG. 14, in an embodiment, housing 80 of sorbent cartridge 100 is closed at one end 82, e.g., the fluid outlet end, and openable at the other end via a lid or cap 84, e.g., the fluid inlet end, such that the user (e.g., patient 12, 112, caregiver, clinician or technician) in one embodiment only has to (i) open one side of cartridge 100 to remove all inner sorbent casings, e.g., casings 106 and 108, (ii) condition the casings 106 and 108, to be reused, (iii) replace the casings to be discarded, (iv) rinse housing 80 itself, (v) reinsert the refurbished casings, e.g., casings 106 and 108, and new casings into rinsed housing 80, and (vi) close the lid or cap 84 onto the open end of housing 80.

In various embodiments, inlet lid or cap 84 of the opened end may thread onto the remainder of cartridge housing 80 via threads 86 or translate onto the remainder of housing 80 and be held removeably fixed to housing via releasable clips or latches 88, such as spring clips or latches. In either case, an o-ring seal 90 may be provided between lid or cap 84 and housing 80, which is compressed when lid or cap 84 is fitted to housing 80. Further, in either case it is contemplated that the action of applying the lid or cap 84 to the remainder of the housing 80 in turn compresses the sorbent casings 94, 96, 102, 106, 108, 104 and 98 together, compressing seals 92 (e.g., o-ring seals) between the casings, such that patient effluent cannot leak between the casings and the inner cartridge. Seals 92 as illustrated may be captured and carried by the casings for ease of handling when the casings are removed from the sorbent cartridge. Exit end casing 98 may have or capture seals 92 on both sides, wherein the seal on the downstream side seals against closed end 82. Alternatively, closed end 82 includes a seal 92 for sealing against exit end casing 98. Seal 92 of inlet end casing 94 in an embodiment seals against an inside of cap 84.

In FIG. 14, housing 80 of sorbent cartridge 100 holds seven casings, including a mechanical filter casing 94, followed by inlet activated carbon and filter casing 96, followed by urease casing 102, followed by H⁺ZP casing 106, followed by Na⁺ZP casing 108 (or casings 106 and 108 could be placed in parallel as illustrated above), followed by anion exchange resin casing 104, followed by outlet activated carbon and filter casing 98. Sorbent cartridge 100 alternatively holds more or less and/or different casings and/or in different orders.

The casings as illustrated are slightly conical in shape and fit together in logical order and orientation to form an overall conical shape, which is the only shape that will fit into like sized and shaped conical housing 80. As mentioned above, sorbent cartridge 100 is configured such that threading or compressing lid or cap 84 onto the remainder of housing 80 compresses (i) seal 90 between lid or cap 84 and the remainder of housing 80 and (ii) seals 92 between casings 94, 96, 102, 106, 108, 104 and 98 (and casing 94 to lid or cap 84 and casing 98 to closed end 82).

In the illustrated embodiment, cap 84 includes an inlet 76 for used dialysis fluid, an initial batch of dialysis fluid, or water needing purification. Closed end 82 of housing 80 includes an outlet 78 for outputting cleansed dialysis fluid (or water). Seals 92 ensure that fluid entering through inlet 76 cannot flow around the outside of the casings between the casings and housing 80. Inlet 76 and outlet 78 may be of the same or different type, including a straight or tapered port to which a tube compression fits, a luer fitting, a threaded fitting, or a ferruled compression fitting. FIG. 14 also illustrates that the circular inlet and outlet faces of casings 94, 96, 102, 106, 108, 104 and 98, within seals 92, may each be made of a mesh material (same or different mesh sizes for the different casings) that allow fluid to flow through the faces, but that trap the sorbent or filter material located within the casings. The mesh material also allows at least some of the casings to be regenerated after use.

The onsite operation may be performed in a dialysis clinic, at a hospital, or at a patient's home, for example. At a clinic, the sorbent casing removal and replacement may be performed by a clinician or technician. At a hospital, the sorbent casing removal and replacement may be performed by a nurse or technician. At home, the sorbent casing removal and replacement may be performed by patient 12, 112 or a caregiver for the patient.

Figure 15:
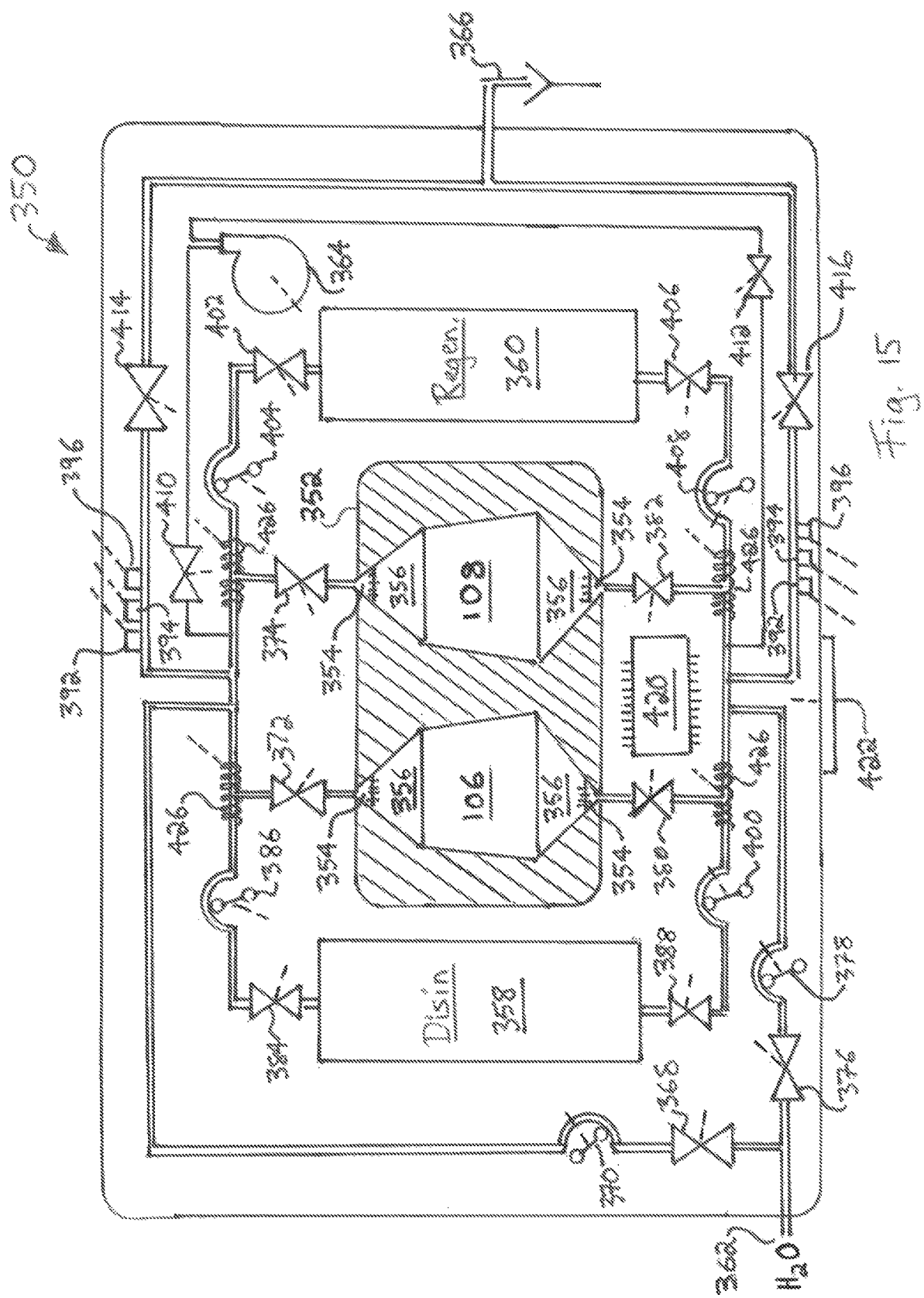
FIG. 15 is a fluid schematic view of one embodiment of an onsite sorbent casing refurbishing device of the present disclosure.

Referring now to FIG. 15, it is further contemplated to provide at the clinic, hospital, or patient's home one or more sorbent conditioning or refurbishing device 350. Device 350 may be configured to condition or refurbish (i) one sorbent casing at a time, (ii) multiple sorbent casings of a same type at the same time, (iii) multiple sorbent casings of different types at the same time (as illustrated in FIG. 15), (iv) multiple sorbent casings of a same type sequentially, or (v) multiple sorbent casings of different types sequentially. Sorbent conditioning or refurbishing device 350 accepts the one or more sorbent casing 106, 108 in a sealed manner, conditions or refurbishes the one or more sorbent casing according to any of the implementations discussed above for the onsite primary embodiment, and informs the user or patient 12, 112 when the casing is ready to be removed from the conditioning or refurbishing device and reused within housing 80 of sorbent cartridge 100.

In the illustrated embodiment, user or patient 12, 112 loads sorbent casings 106 and 108 into a cleaning chamber 352, which surrounds the casings and holds them in a restrained manner. Although not illustrated, cleaning chamber 352 my provide a hinged lid that user or patient 12, 112 opens to insert or remove casings 106 and 108. The lid is lockable to condition or refurbish the casings. In an embodiment, one or more sensor, such as a contact switch or proximity sensor is provided to ensure that the lid is locked prior to any fluid flow through cleaning chamber 352. In the illustrated embodiment, cleaning chamber 352 provides tapered or conical insert areas to form fit casings 106 and 108, prevent leakage and to ensure that the casings are placed into cleaning chamber 352 in a desired orientation. In the illustrated embodiment, casings 106 and 108 are positioned so as to be tapered in the same direction but could alternatively be positioned so as to be tapered in opposite or otherwise different directions. Cleaning chamber 352 introduces fluids to and recovers fluids from casings 106 and 108 via nozzles 354 and funneled openings 356, so that the fluid is spread to the entire intended surface of the casings.

At least one source of disinfectant 358 and at least one source of reneration fluid 360 are provided and in one embodiment housed within sorbent conditioning or refurbishing device 350. In alternative embodiments one or both of sources 358 or 360 is/are located outside device 350. Disinfectant 358 and regenerated fluid 360 may be any of any type described herein. Device 350 in the illustrated embodiment is further provided with a water, e.g., tap water, hookup 362 and a hot air blower 364. Fluids are drained to a drain 366.

In the illustrated embodiment, conditioning or refurbishing device 350 is arranged fluidly such that disinfectant 358, reneration fluid 360, water from hookup 362 and hot air from blower 364 may be directed to casings 106 and 108 in either normal flow or reverse flow directions. In alternative embodiments, some of these flow paths may be eliminated as desired.

As illustrated: (i) valve 368 and pump 370 enable water to be selectively delivered to the upper side of cleaning chamber 352, wherein valves 372 and 374 determine which (or both) casings 106 and 108 receive pressurized water from above; (ii) valve 376 and pump 378 enable water to be selectively delivered to the lower side of cleaning chamber 352, wherein valves 380 and 382 determine which (or both) casings 106 and 108 receive pressurized water from below; (iii) valve 384 and pump 386 enable disinfectant to be selectively delivered to the upper side of cleaning chamber 352, wherein valves 372 and 374 determine which (or both) casings 106 and 108 receive pressurized disinfectant from above; (iv) valve 388 and pump 400 enable disinfectant to be selectively delivered to the lower side of cleaning chamber 352, wherein valves 380 and 382 determine which (or both) casings 106 and 108 receive pressurized disinfectant from below; (v) valve 402 and pump 404 enable regeneration fluid to be selectively delivered to the upper side of cleaning chamber 352, wherein valves 372 and 374 determine which (or both) casings 106 and 108 receive pressurized regeneration fluid from above; (vi) valve 406 and pump 408 enable regeneration fluid to be selectively delivered to the lower side of cleaning chamber 352, wherein valves 380 and 382 determine which (or both) casings 106 and 108 receive pressurized regeneration fluid from below; (vii) valves 410 and 412 selectively allow hot air from blower 364 to be delivered to the upper and lower sides of cleaning chamber 352, respectively, wherein valves 372, 374, 380 and 382 determine which one or both casings 106 and 108 receive hot air for drying; and (viii) drain valves 414 and 416 in combination with valves 372, 374, 380 and 382 selectively allow any fluid or hot air to be exhausted from either casing 106 and 108 and from upper and/or lower sides, respectively, of cleaning chamber 352.

As illustrated, conductivity sensors 392, temperature sensors 394 and pH sensors 396 are located in strategic locations to sense desired fluid flow characteristics, e.g., to know when to stop a particular fluid flow as described in numerous ones of the implementations discussed above. In the illustrated embodiment, conductivity sensors 392, temperature sensors 394 and pH sensors 396 are located along the branches leading to drain 366. Sensors 392, 394 and 396 include dashed lines indicating power and signal connections to control unit 420.

Sorbent conditioning or refurbishing device 350 is also illustrated as having heating coils 426, which may be electrically resistive heating coils under control of control unit 420. Feedback from temperature sensors 394 to control unit 420 allows a heating algorithm employed by the control unit to determine which heating coils 426 if any to energize to heat the corresponding fluid to a desirted temperature, e.g., up to about 80° C.

In the illustrated embodiment, all pumps, valves, hot air blower 364 and heating coils 426 are operated by a control unit 420 of conditioning or refurbishing device 350 as indicated by the dashed electrical lines. The pumps are illustrated as peristaltic pumps but may alternatively be volumetric or diaphragm pumps, gear pumps or other suitable fluid pump. A user interface 422 operating with control unit 420 is provided to enable user or patient 12, 112 to operate refurbishing device 350. Sensors 392, 394 and 396 likewise output to, and may receive power from, control unit 420.

In alternative embodiments sorbent conditioning or refurbishing device 350 uses less pumps, e.g., (i) a single pump (two total) for each of the upper and lower sides of cleaning chamber 352 to handle all three of water, disinfecting agent and regeneration solution flow, or (ii) a single pump for both of the upper and lower sides of cleaning chamber 352 to handle all three of water, disinfecting agent and regeneration solution flow on both upper and lower sides. Valves are arranged accordingly to selectively allow water, disinfecting agent or regeneration solution flow at a given time.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims. For example, while the specification has concentrated on the regeneration of zirconium sorbent materials, the conditioning or refurbishing device 350, sorbent cartridge 100 and their associated methods of use (including any implementation method 160, 180, 200, 220, 240, 260, 280, 300 and 320) may be applied to other materials that perform the same or similar function as zirconium sorbent materials, such as titanium-based sorbent materials.

The invention is claimed as follows:

1. A medical fluid delivery method comprising:
   providing a sorbent cartridge including zirconium phosphate ("ZP") or zirconium oxide ("ZO") for a treatment; and
   after the treatment, refurbishing the ZP or ZO via
      disinfecting the non-regenerated ZP or ZO using a disinfecting agent,
      regenerating the disinfected ZP or ZO using a sodium based alkaline solution or a sodium salt solution,
      at least one of washing or filtering the disinfected and regenerated ZP or ZO,
      titrating the washed or filtered ZP or ZO until a desired pH is reached in a first effluent from the titrating,
      at least one of washing or filtering the titrated ZP or ZO until a desired conductivity is reached in a second effluent from the washing or filtering,
      drying the rewashed or refiltered ZP or ZO, and
      sieving the dried ZP or ZO.

2. The medical fluid delivery method of claim 1, wherein at least one of (a) the sodium based alkaline solution or a sodium salt solution is NaOH, NaHCO$_3$, Na$_2$CO$_3$ or NaCl or (b) the disinfecting agent (i) is sodium based, such as including NaOCl, (ii) is hydrogen based, such as including HOCl, or (iii) includes isopropyl alcohol ("IPA").

3. The medical fluid delivery method of claim 1, wherein the desired pH is between and including 5.5 to 8.5.

4. The medical fluid delivery method of claim 1, wherein the desired conductivity is below 50 μS/cm.

5. The medical fluid delivery method of claim 1, wherein refurbishing the ZP or ZO includes combining ZP or ZO removed from multiple sorbent cartridges before disinfection.

6. A medical fluid delivery method comprising:
   providing a sorbent cartridge including zirconium phosphate ("ZP") or zirconium oxide ("ZO") for a treatment; and
   after the treatment, refurbishing the ZP or ZO via
      disinfecting the non-regenerated ZP or ZO using a disinfecting agent,
      regenerating the disinfected ZP or ZO using a sodium based alkaline solution or a sodium salt solution,
      at least one of washing or filtering the disinfected and regenerated ZP or ZO,
      drying the washed or filtered ZP or ZO, and
      sieving the dried ZP or ZO.

7. The medical fluid delivery method of claim 6, wherein at least one of (a) the sodium based alkaline solution or a sodium salt solution is NaOH, NaHCO$_3$, Na$_2$CO$_3$ or NaCl or (b) the disinfecting agent (i) is sodium based, such as including NaOCl, (ii) is hydrogen based, such as including HOCl, or (iii) includes isopropyl alcohol ("IPA").

8. The medical fluid delivery method of claim 7, wherein refurbishing the ZP or ZO includes combining ZP or ZO removed from multiple sorbent cartridges before disinfection.

* * * * *